(12) United States Patent
Omoto et al.

(10) Patent No.: US 9,237,837 B2
(45) Date of Patent: Jan. 19, 2016

(54) INSERTION DEVICE WITH THE OPERATION INPUT UNIT

(71) Applicant: OLYMPUS CORPORATION, Tokyo (JP)

(72) Inventors: Keijiro Omoto, Hachioji (JP); Hiroki Moriyama, Akishima (JP); Yasuhiro Okamoto, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/061,187

(22) Filed: Oct. 23, 2013

(65) Prior Publication Data

US 2014/0135580 A1    May 15, 2014

Related U.S. Application Data

(63) Continuation of application No. PCT/JP2013/055186, filed on Feb. 27, 2013.

(30) Foreign Application Priority Data

Feb. 27, 2012 (JP) .................................. 2012-040407
Nov. 1, 2012 (JP) .................................. 2012-241745

(51) Int. Cl.
*A61B 1/00* (2006.01)
*A61B 1/005* (2006.01)
(Continued)

(52) U.S. Cl.
CPC .............. *A61B 1/0052* (2013.01); *A61B 1/0016* (2013.01); *A61B 1/00039* (2013.01); *G02B 23/2476* (2013.01)

(58) Field of Classification Search
CPC .. A61B 1/0016; A61B 1/0052; A61B 1/0055; A61B 1/00066
USPC ......... 600/104, 146, 148, 150, 106, 147, 149; 348/45, 65; 396/17
See application file for complete search history.

(56) References Cited

U.S. PATENT DOCUMENTS

| 5,618,294 A | 4/1997 | Aust et al. |
| 5,658,238 A | 8/1997 | Suzuki et al. |
| 2007/0255103 A1 | 11/2007 | Maruyama |

(Continued)

FOREIGN PATENT DOCUMENTS

| EP | 1 839 552 A1 | 10/2007 |
| JP | A-2006-192201 | 7/2006 |

(Continued)

OTHER PUBLICATIONS

Machine Translation of JP2009-219822, 18 pages.*

(Continued)

*Primary Examiner* — Anhtuan T Nguyen
*Assistant Examiner* — Timothy J Neal
(74) *Attorney, Agent, or Firm* — Oliff PLC

(57) ABSTRACT

An insertion device sets engage range which it prescribed in return power to the neutral position by elastic force of the spring and rotation resistance force by the slide power by elastic member for dial portion performing curving operation of a curving portion. If a rotary angle is beyond an engage range, the dial part lets a rotary point of view to order return in an engage range and, if there is a rotary angle in an engage range, the dial part keeps a target part in an observation field of vision.

3 Claims, 35 Drawing Sheets

(51) Int. Cl.
*A61B 1/04* (2006.01)
*G02B 23/24* (2006.01)

(56) References Cited

U.S. PATENT DOCUMENTS

2007/0265500 A1   11/2007   Koitabashi et al.
2011/0088498 A1*  4/2011    Ettwein et al. ............. 74/479.01

FOREIGN PATENT DOCUMENTS

| JP | A-2008-264107 | 11/2008 |
| JP | A-2009-219822 | 10/2009 |
| JP | A-2009-226125 | 10/2009 |
| WO | 2010/066789 A1 | 6/2010 |

OTHER PUBLICATIONS

International Search Report issued in International Patent Application No. PCT/JP2013/055186 dated Apr. 16, 2013 (w/ translation).
Feb. 27, 2013 International Preliminary Report on Patentability issued in International Patent Application No. PCT/JP2013/055186 (translation only).
Sep. 12, 2014 International Preliminary Report on Patentability issued in International Patent Application No. PCT/JP2013/055186 (translation only).
Sep. 28, 2015 Office Action issued in Chinese Patent Application No. 201380011242.4.
Oct. 14, 2015 Office Action issued in European Patent Application No. 13755253.5.

* cited by examiner

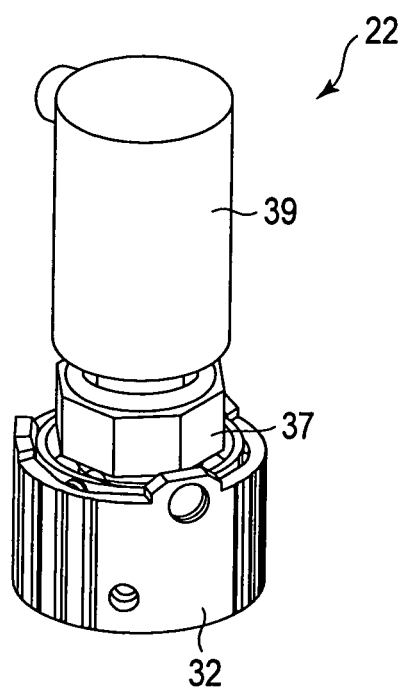
F I G. 6

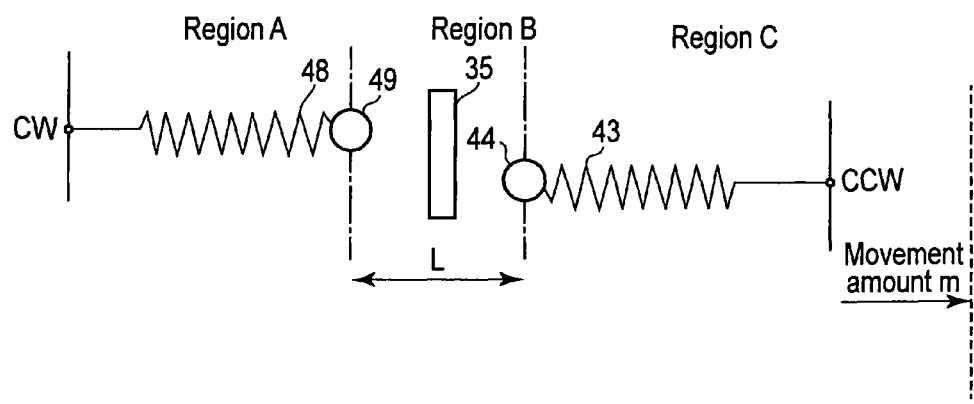
F I G. 11A
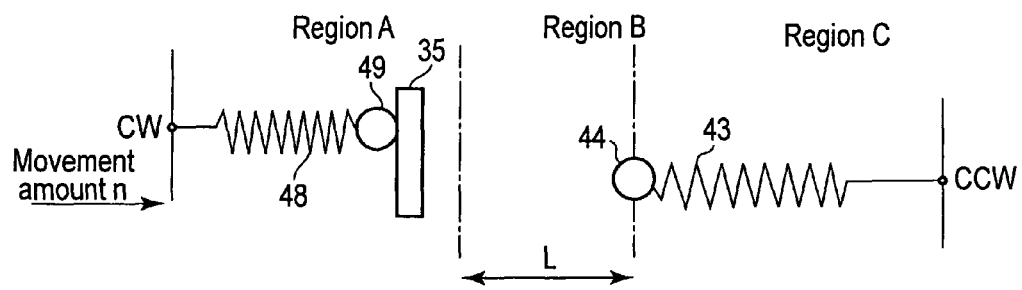
F I G. 11B

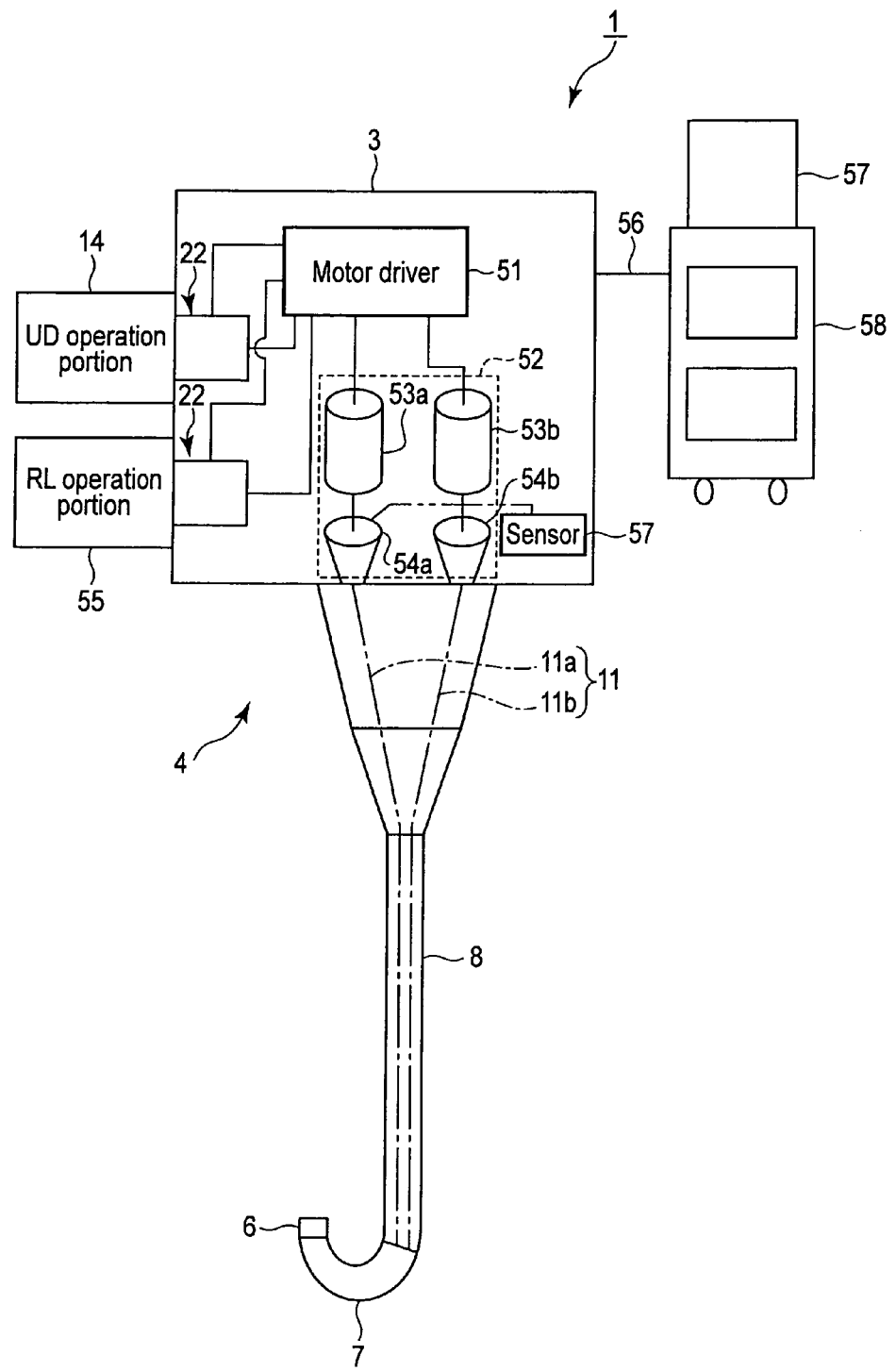
F I G. 14

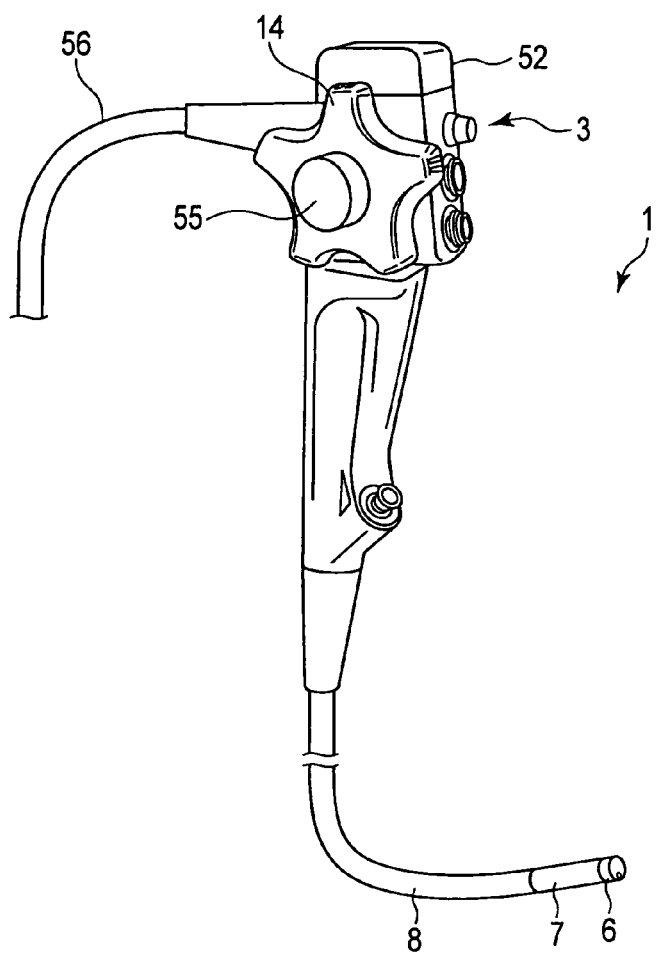
F I G. 15A
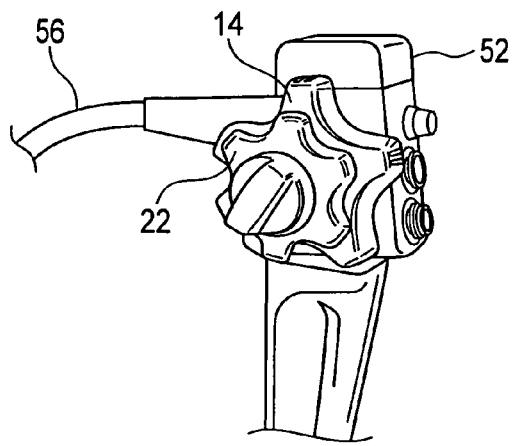
F I G. 15B

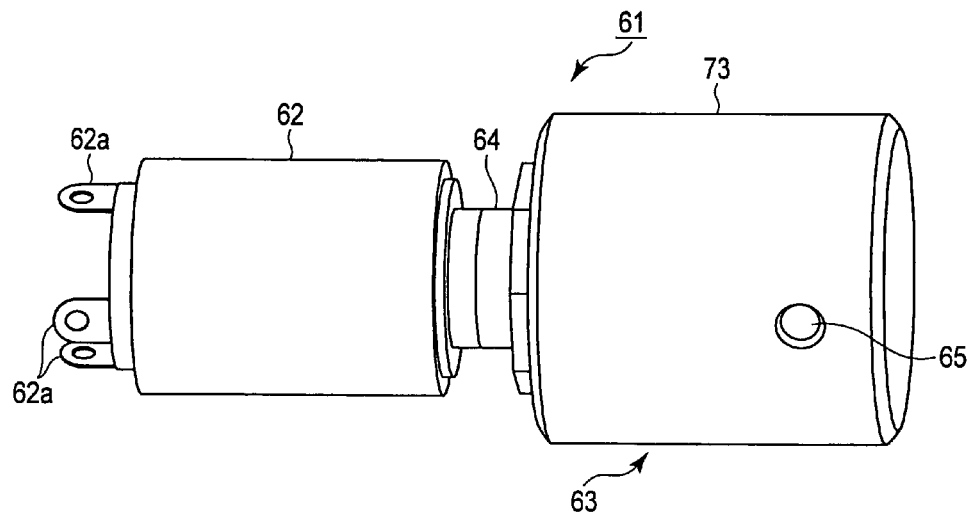
F I G. 16
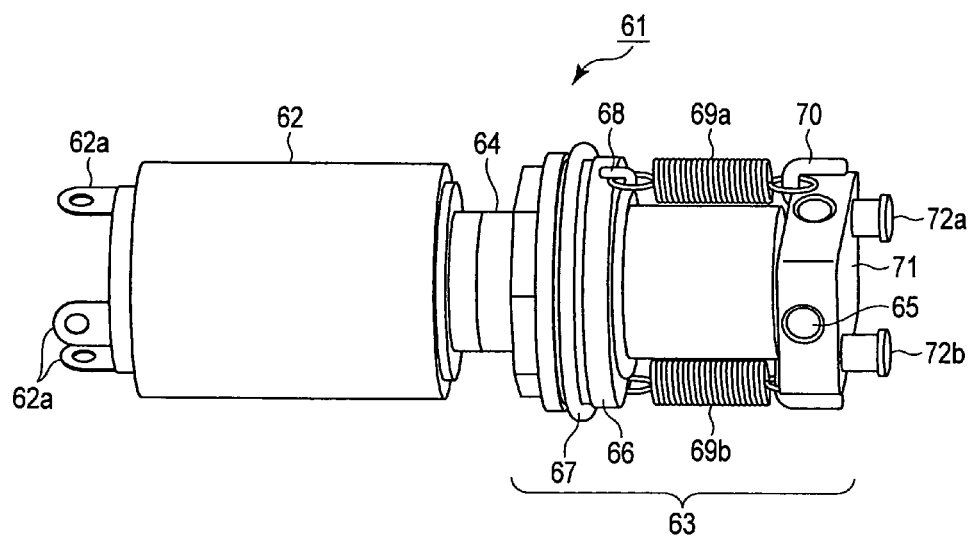
F I G. 17

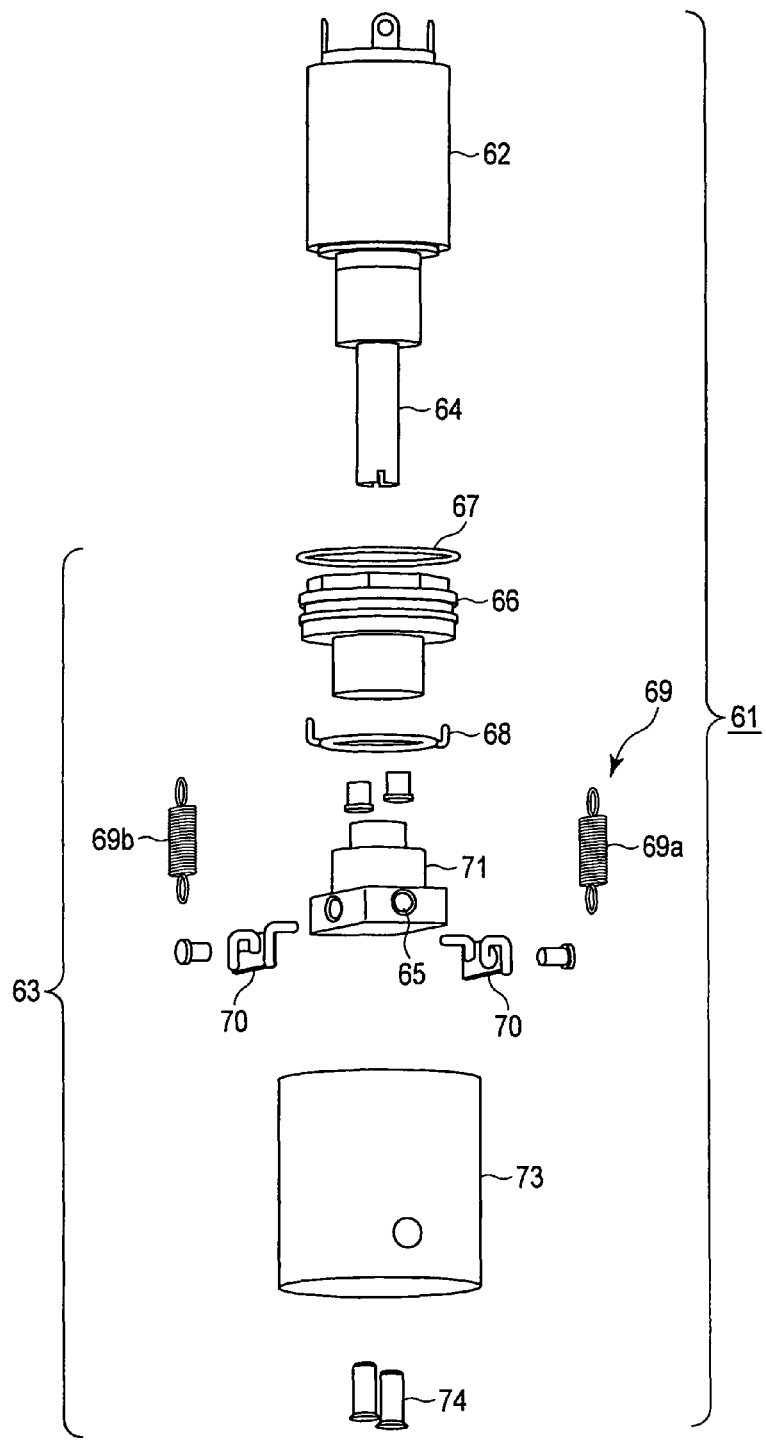
F I G. 18

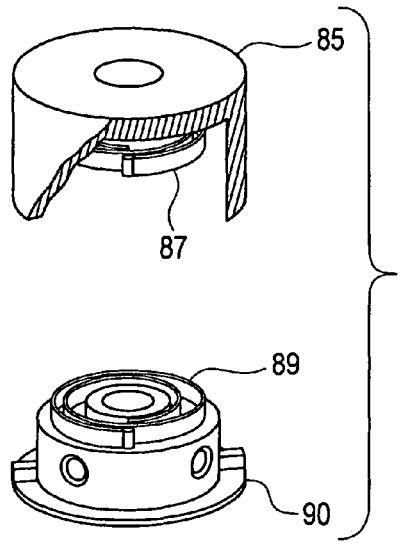
F I G. 22
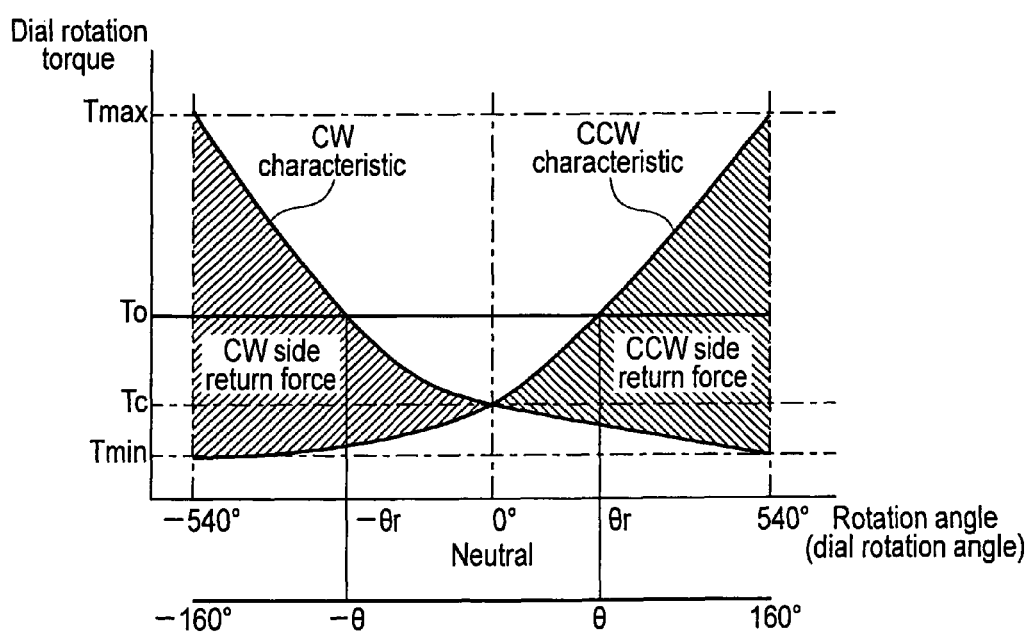
F I G. 23

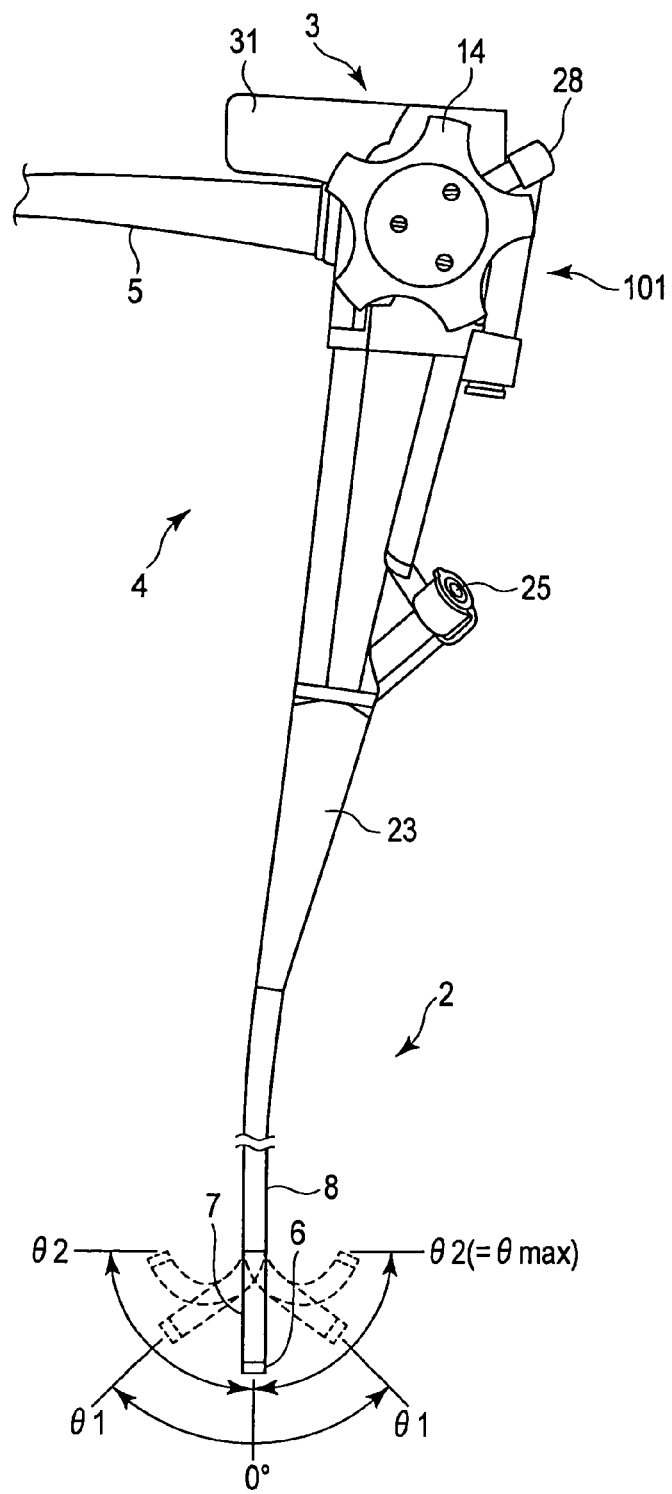
F I G. 24

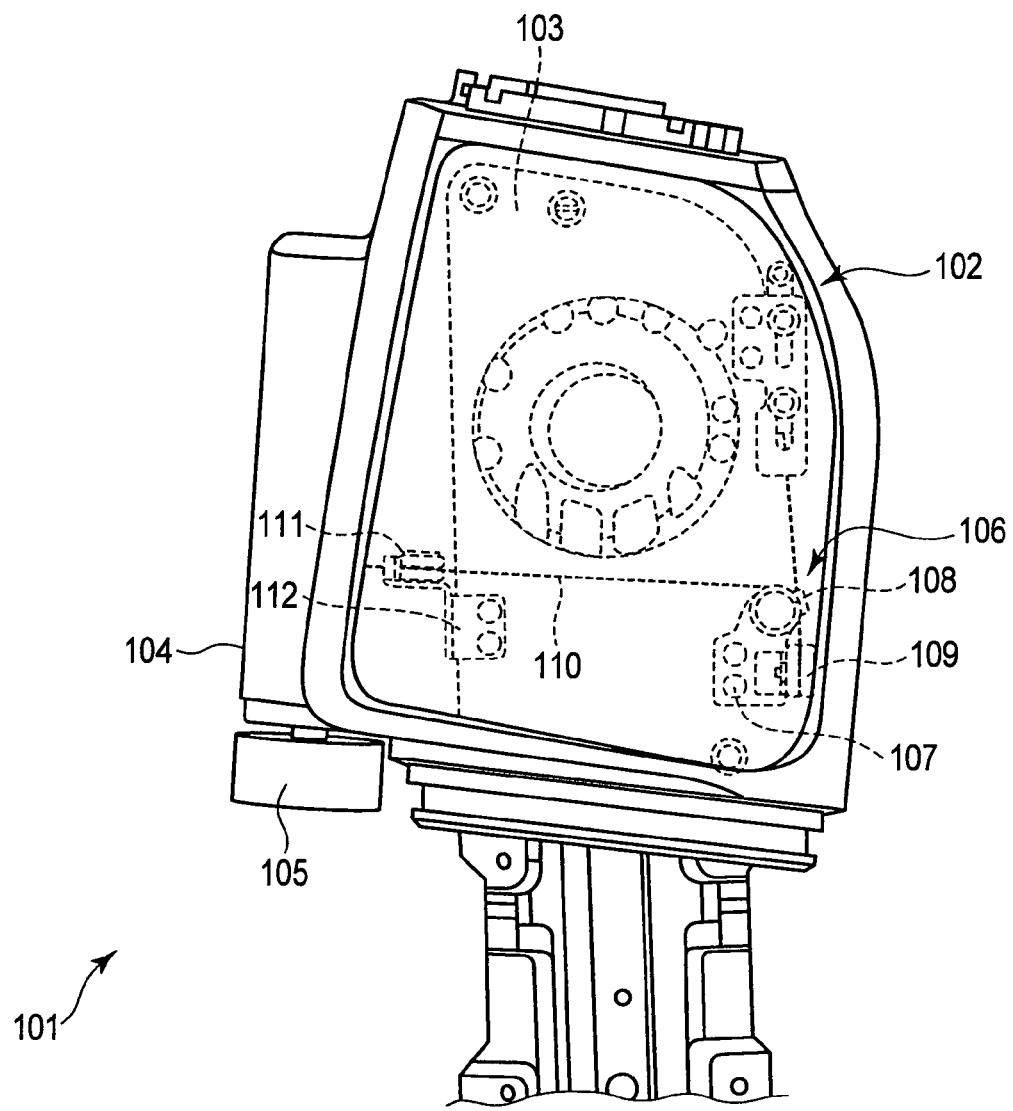
F I G. 25

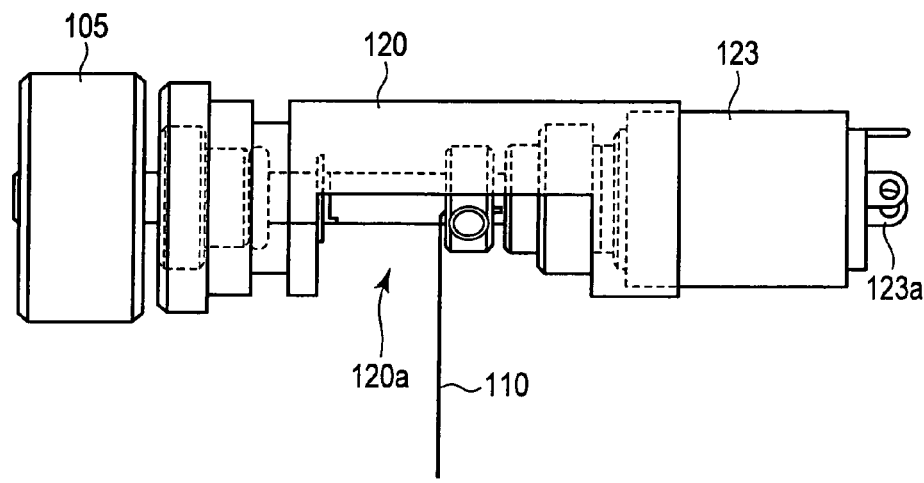
F I G. 28A
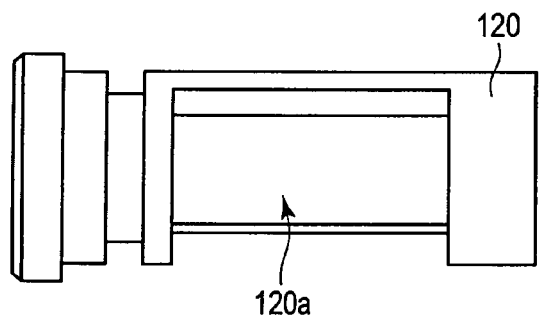
F I G. 28B
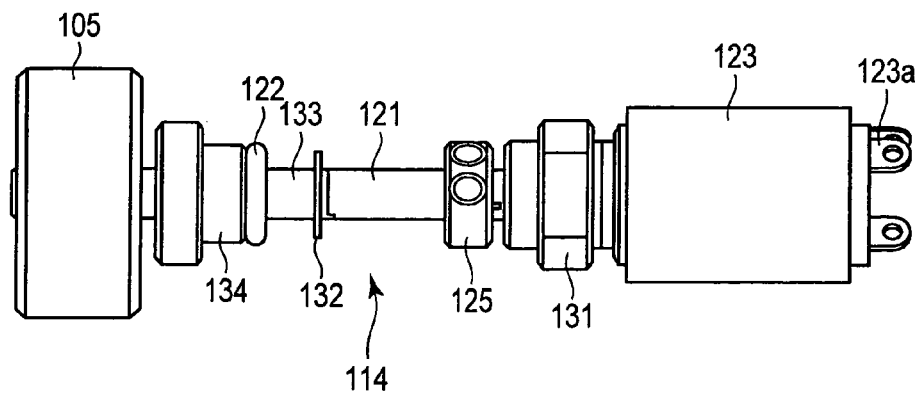
F I G. 28C

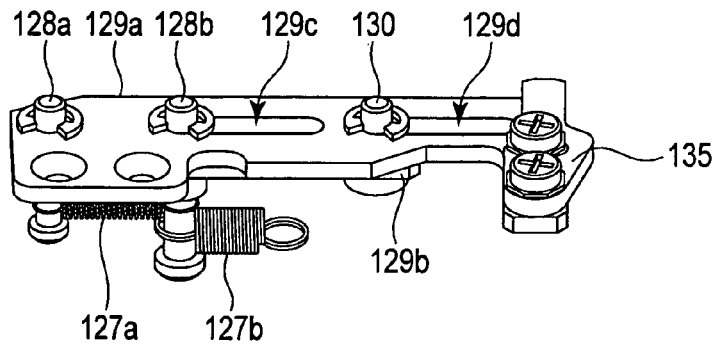
F I G. 30A
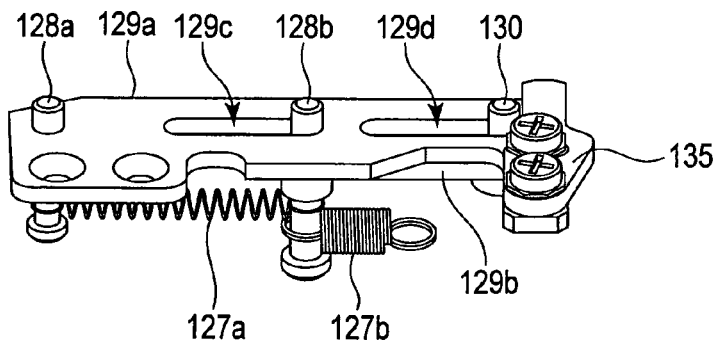
F I G. 30B
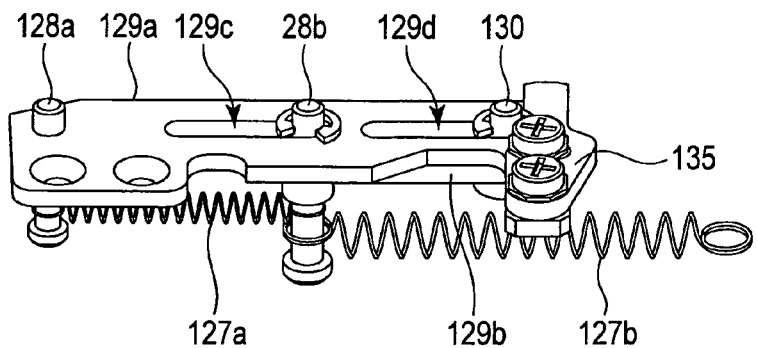
F I G. 30C

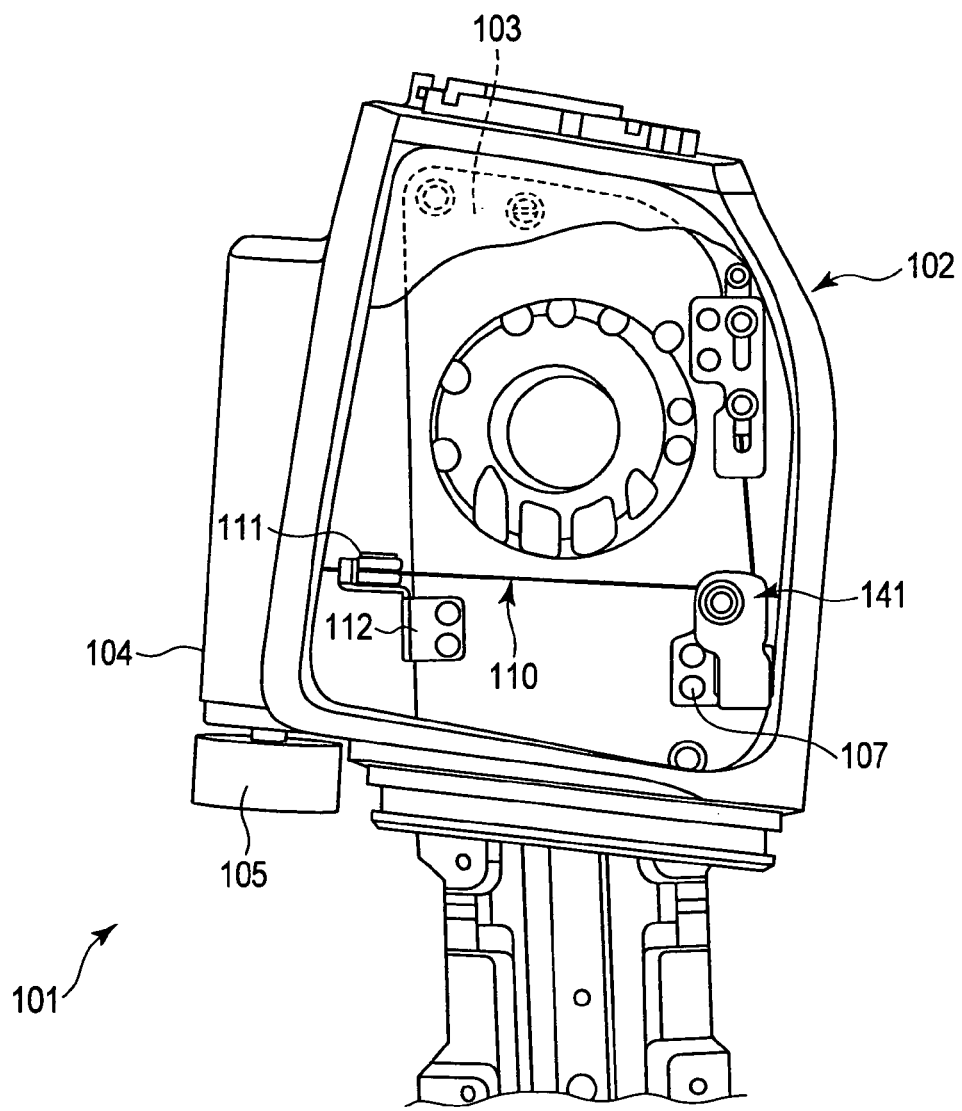
F I G. 31

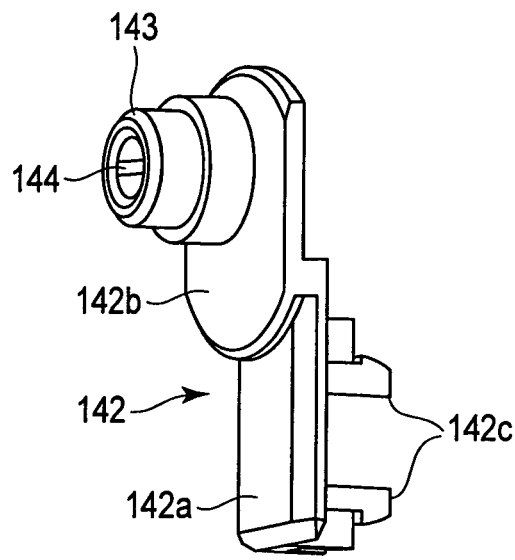
F I G. 32C
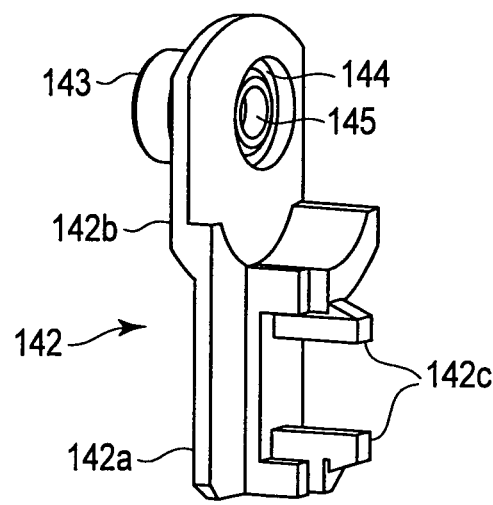
F I G. 32D

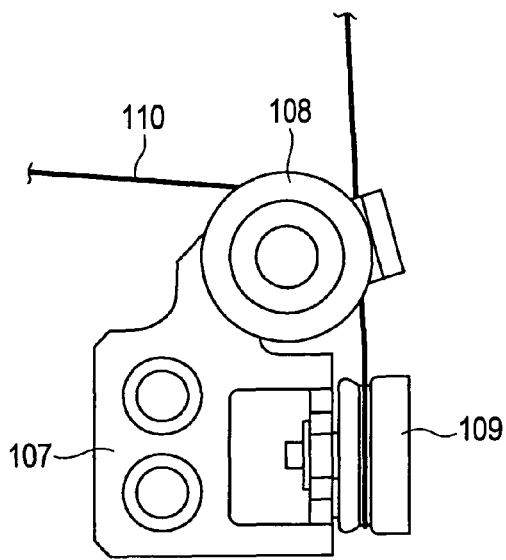
F I G. 32E
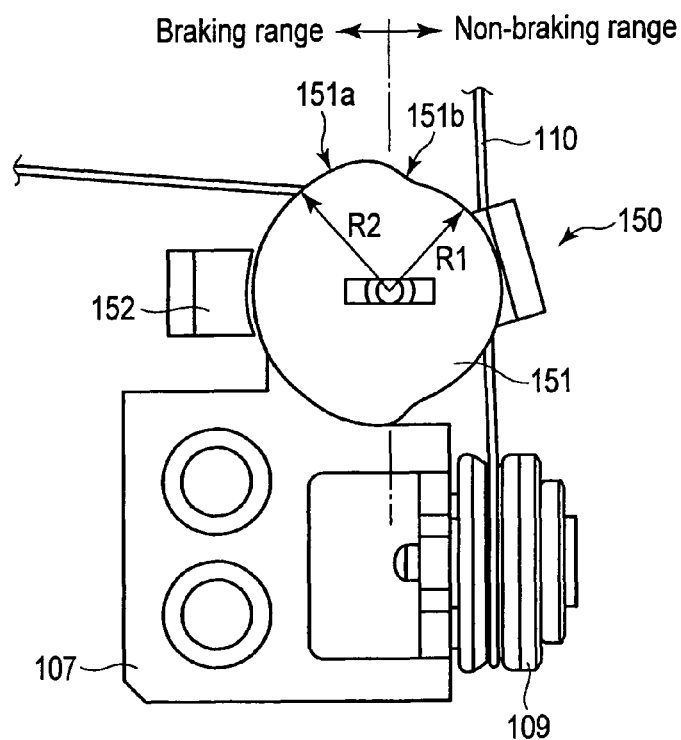
F I G. 33A

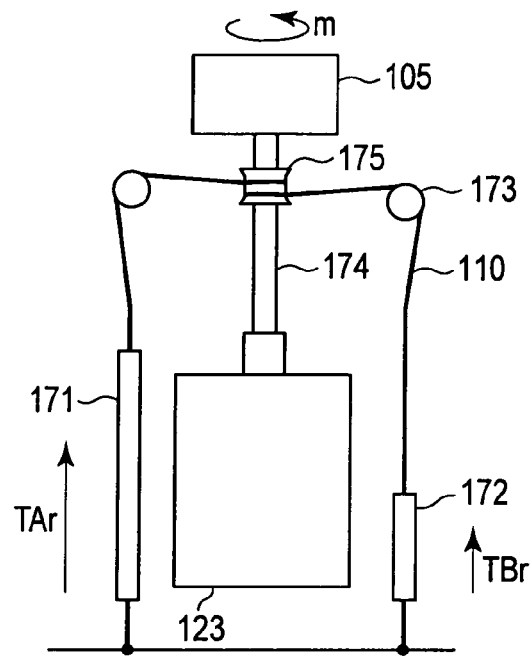
F I G. 36B
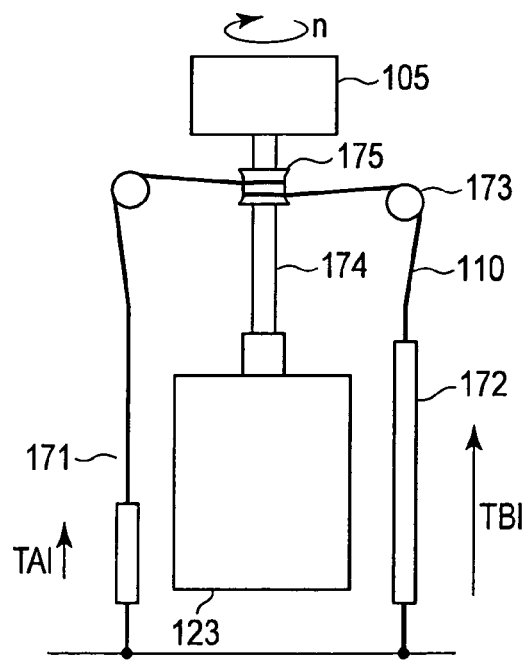
F I G. 36C

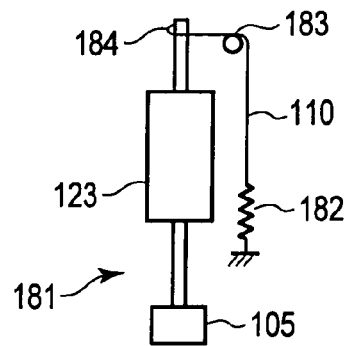
F I G. 37
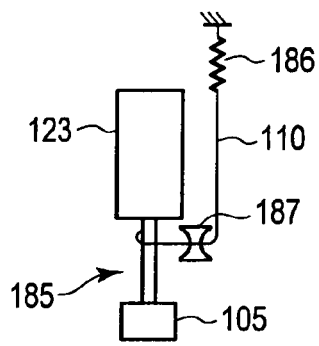
F I G. 38
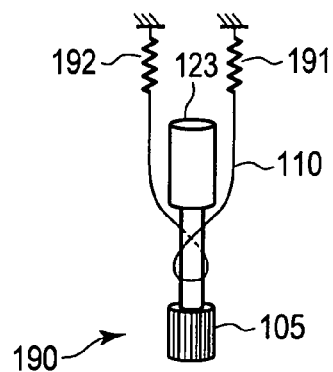
F I G. 39

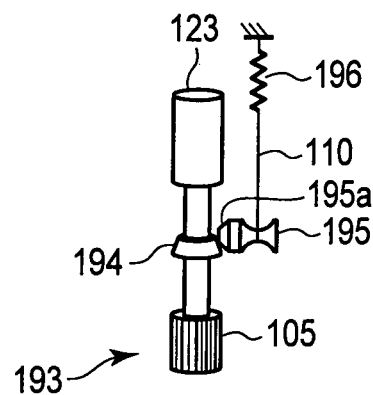
F I G. 40
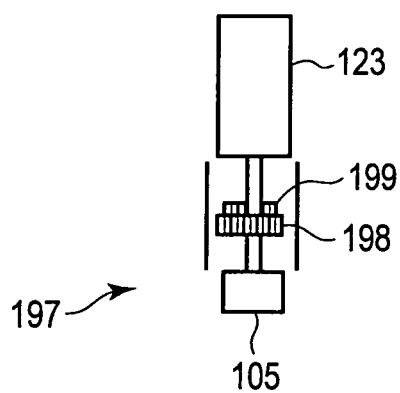
F I G. 41

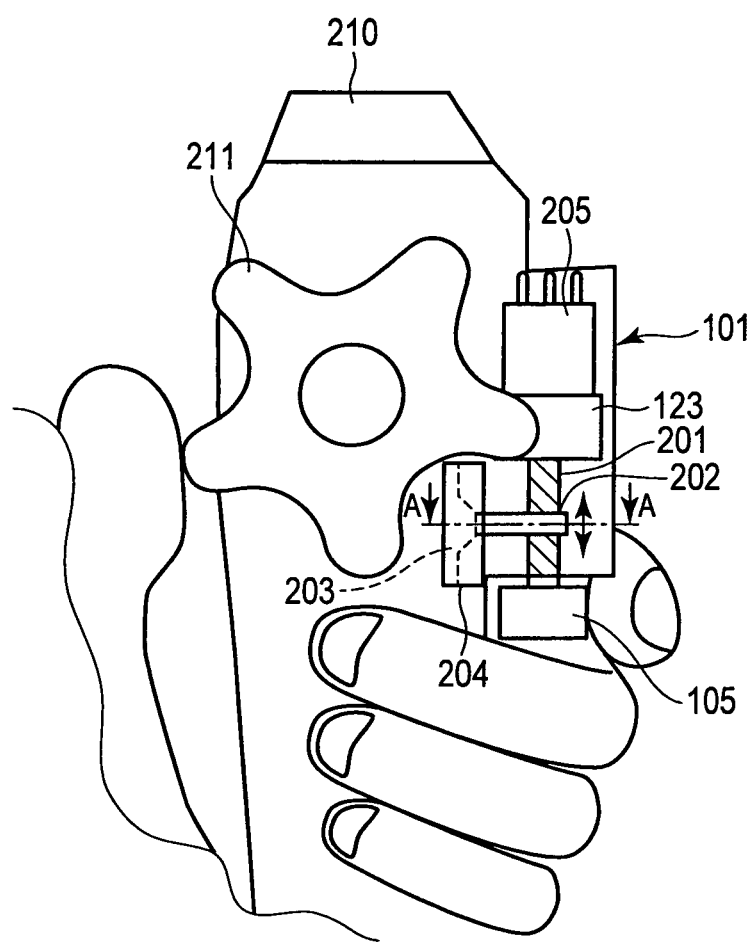
F I G. 42A

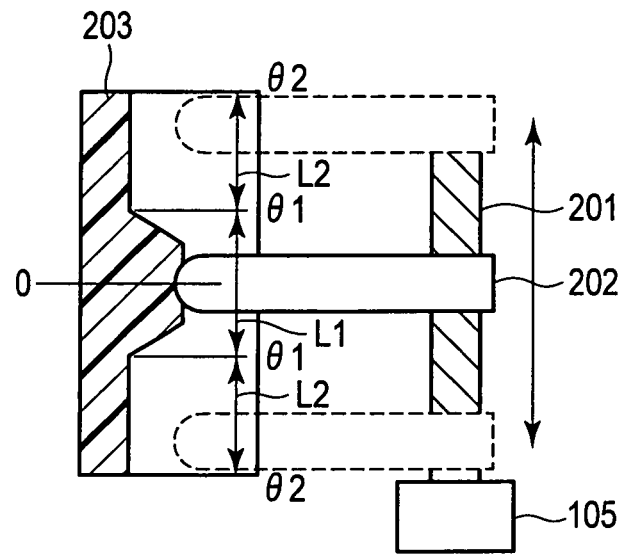
F I G. 42B
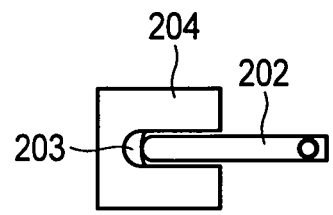
[A-A]
F I G. 42C

INSERTION DEVICE WITH THE OPERATION INPUT UNIT

CROSS-REFERENCE TO RELATED APPLICATIONS

This is a Continuation Application of PCT Application No. PCT/JP2012/055186, filed Feb. 27, 2013, which was published under PCT Article 21(2) in Japanese.

This application is based upon and claims the benefit of priority from prior the Japanese Patent Application No. 2012-040407, filed Feb. 27, 2012; and No. 2012-241745 filed Nov. 1, 2012 the entire contents of both of which are incorporated herein by references.

BACKGROUND OF THE INVENTION

1. Field of the Invention

The present invention relates to an insertion device comprising an operation input portion which maintains a curving state of a curving portion even if a hand is taken off during operation and which returns to a range including a neutral position beyond a predetermined curving operation range.

2. Description of the Related Art

In general, there is an insertion device which comes into a body cavity or into a duct having curved parts for visual observation. This insertion device includes a medical or industrial endoscope device comprising an insertion portion which is elongated and flexible and which is provided with a curving portion at its distal end. For example, when the medical endoscope device is used for a diagnosis or surgery of the body cavity, an operation portion is operated to drive the curving portion provided on the distal side of the insertion portion into the body cavity while vertically and horizontally curving the curving portion.

For example, in an endoscope device disclosed in Patent Literature 1 (Jpn. Pat. Appln. KOKAI Publication No. 2008-264107), a curving portion is coupled to a curving operation portion by an operation wire, and this operation wire is pulled by the curving operation portion to bend the curving portion. In this endoscope device, a curving operation dial which is rotationally operated is used as the curving operation portion, and an operation is input by one (360°) or more rotational operations of the dial.

If the operation dial is configured to be rotated on or more times (360° or more) as in Patent Literature 1 described above, an operator makes a round trip to the rotation direction of the operation dial and then repeats the rotational operations. As a result, the operator finds it difficult to find an original neutral position and know the actual curving state of the curving portion. In this case, the operator returns the operation dial to the neutral position under visual observation, and then again performs a curving operation.

Accordingly, Patent Literature 2 (Jpn. Pat. Appln. KOKAI Publication No. 2009-226125) has suggested an operation portion of an endoscope device comprising an urging mechanism which returns an UD (up/down) or RL (right/left) operation dial of the operation portion to a neutral position. The operation portion has the urging mechanism in which two spiral springs that are wound in opposite directions face each other and have their inner ends attached to a rotating shaft of the operation dial and their outer ends attached to a fixed member. In this urging mechanism, the elastic forces (urging forces) of the springs are adjusted to balance at the neutral position (initial position: a curving portion linearly extends) of the operation dial. If the operation dial is rotated in this configuration, one of the springs expands its spiral, while the other spring shrinks its spiral. As a result of these actions, the operation dial returns to the original neutral position which is the initial position in response to each of the springs when a hand is taken off the operation dial.

BRIEF SUMMARY OF THE INVENTION

According to an embodiment of the present invention, there is provided an insertion device comprising a curving portion which is provided in an insertion portion to be inserted into a body cavity and which is curvable between a linear state and a curving state at a maximum curving angle; an operation input portion for an operator to operate the curving portion; an operation input unit which is actuated to curve the curving portion in accordance with the operation of the operation input portion; and an elastic member which is deformed in accordance with the actuation of the operation input unit, the elastic member generating elastic force for the operation input unit to return the curving portion to the linear state when the curving portion is curved at a predetermined angle or more, the elastic force having no effect on the operation input unit when the curving portion is at the predetermined angle or less.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 6 is a perspective view of an RL operation input unit;

FIG. 11A is a schematic view showing spiral grooves of a CW lead unit and the CCW lead unit in a linearly extended state;

FIG. 11B is a schematic view showing returning elastic force applied when a lever is moved in FIG. 11A;

FIG. 14 is a block diagram showing the general configuration of an endoscope device according to a second embodiment;

FIG. 15A is a diagram showing a first modification of an operation dial of an endoscope body according to the second embodiment;

FIG. 15B is a diagram showing a second modification of the operation dial of the endoscope body according to the second embodiment;

FIG. 16 is a diagram showing the external configuration of an operation input unit;

FIG. 17 is a diagram showing the internal configuration of the operation input unit without a case;

FIG. 18 is a diagram showing the assembly configuration of the operation input unit;

FIG. 22 is a diagram illustrating how to set a spiral spring to a cylindrical cap and a fixed plate;

FIG. 23 is a graph showing a neutral return characteristic according to the third embodiment;

FIG. 24 is a diagram showing the external configuration of an endoscope body according to a fourth embodiment;

FIG. 25 is an arrangement/configuration example of an input operation portion and a neutral return mechanism in an input unit located apart from an operation portion;

FIG. 28A is a diagram showing a detailed configuration of the input operation portion;

FIG. 28B is a diagram showing the appearance of a bracket of an exterior;

FIG. 28C is a diagram showing the configuration of an operator body;

FIG. 30A is a diagram showing the state of the neutral return mechanism in which the operation dial inhibits the slack of a wire in the vicinity of a neutral position;

FIG. 30B is a diagram showing how the neutral return mechanism located within an engage range around the neutral position does not return due to braking force applied to the operation dial;

FIG. 30C is a diagram showing how the operation dial is rotated so that the neutral return mechanism returns due to elastic force surpassing the braking force;

FIG. 31 is a diagram showing a conceptual configuration of an input unit equipped with a braking mechanism according to a fifth embodiment;

FIG. 32C is a diagram showing the braking mechanism seen obliquely from above;

FIG. 32D is a diagram showing the braking mechanism seen obliquely from below;

FIG. 32E is a diagram showing the braking mechanism seen from the rear;

FIG. 33A is a diagram showing a braking mechanism according to a sixth embodiment seen from the front;

FIG. 36B is a diagram showing the state of an elastic member when an operation dial shown in FIG. 36A is rotated in an m-direction;

FIG. 36C is a diagram showing the state of the elastic member when the operation dial shown in FIG. 36A is rotated in an n-direction;

FIG. 37 is a diagram showing a conceptual configuration of a neutral return mechanism provided in an operation portion according to a tenth embodiment;

FIG. 38 is a diagram showing a conceptual configuration of a neutral return mechanism provided in an operation portion according to an eleventh embodiment;

FIG. 39 is a diagram showing a conceptual configuration of a neutral return mechanism provided in an operation portion according to a twelfth embodiment;

FIG. 40 is a diagram showing a conceptual configuration of a neutral return mechanism provided in an operation portion according to a thirteenth embodiment;

FIG. 41 is a diagram showing a conceptual configuration of an input operation portion of an input unit according to a fourteenth embodiment;

FIG. 42A is a diagram showing a conceptual configuration of a neutral return mechanism provided in an operation portion according to a fifteenth embodiment;

FIG. 42B is a diagram showing a return range when the operation dial is rotated; and FIG. 42C is a diagram showing a section [A-A] of FIG. 42A.

DETAILED DESCRIPTION OF THE PREFERRED EMBODIMENT

Hereinafter, embodiments of the present invention will be described in detail with reference to the drawings.

First Embodiment

Figure 1:
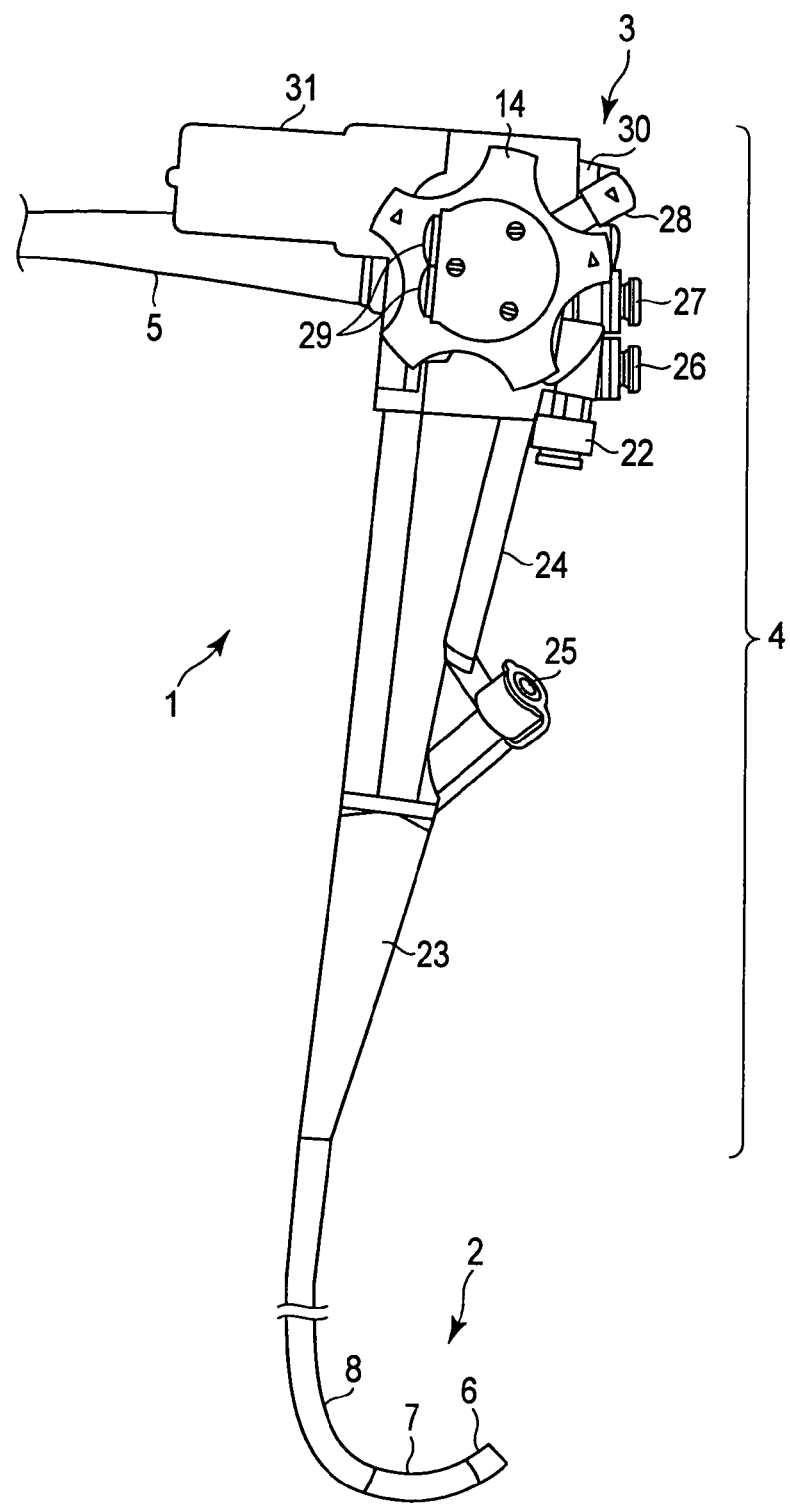
FIG. 1 is a diagram showing the external configuration of an insertion device according to a first embodiment.

FIG. 1 is a diagram showing the external configuration of an endoscope device according to the first embodiment of the present invention.

An endoscope device 1 roughly has an insertion portion 2 whose distal side is to be inserted into a body cavity, an endoscope body 4 which is coupled to the proximal side of the insertion portion 2 and which includes an operation portion 3, and a universal cord 5 including, for example, a light guide and a signal cable extending from the endoscope body 4.

As shown in FIG. 14 described later, in the present embodiment, a connector is used to removably connect the endoscope body 4 to devices mounted on a trolley through a universal cord 56 including, for example, a light guide and an electric cable. The devices used include at least a light source device which guides illumination light, a video processor device which converts an image obtained by the endoscope body 4 to a display image signal, and a monitor 57 which displays an image resulting from the image signal output by the video processor device.

The insertion portion 2 is an elongated tubular portion on the distal side of the endoscope to be inserted into, for example, a body cavity. The insertion portion 2 has a distal portion 6 located at the most distal end, a curving portion 7 provided on the proximal side of the distal portion 6, and a long flexible tubular portion 8 provided on the proximal side of the curving portion 7.

The distal portion 6 is a rigid portion which has an outer circumferential surface made of a rigid material such as stainless steel and which is covered with a distal portion cover made of a synthetic resin. Although not shown, there are provided, inside the distal portion 6, an observation optical system including an objective lens disposed on a distal surface, a solid-state image sensing device such as a CCD which forms an optical image obtained from the observation optical system and then converts the optical image to an electric signal, an illumination optical system including an illumination lens disposed on the distal surface, a light guide which guides the illumination light from the light source device to the illumination optical system, and a forceps channel for forceps insertion.

Figure 2:
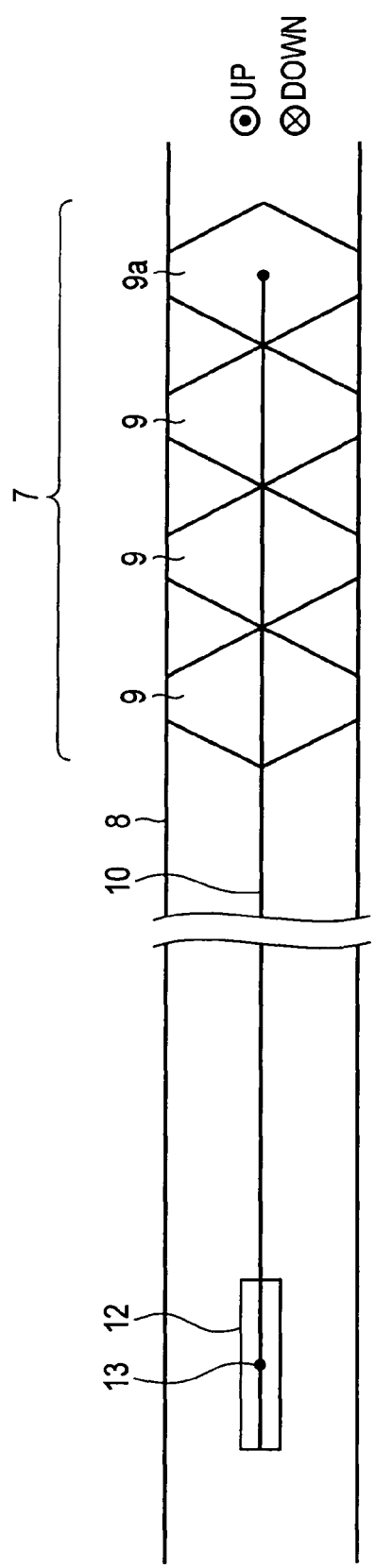
FIG. 2 is a diagram showing the configurations of a curving portion, a flexible tubular portion, and an endoscope device associated with a vertical curving operation of the curving portion according to the first embodiment.
Figure 3:
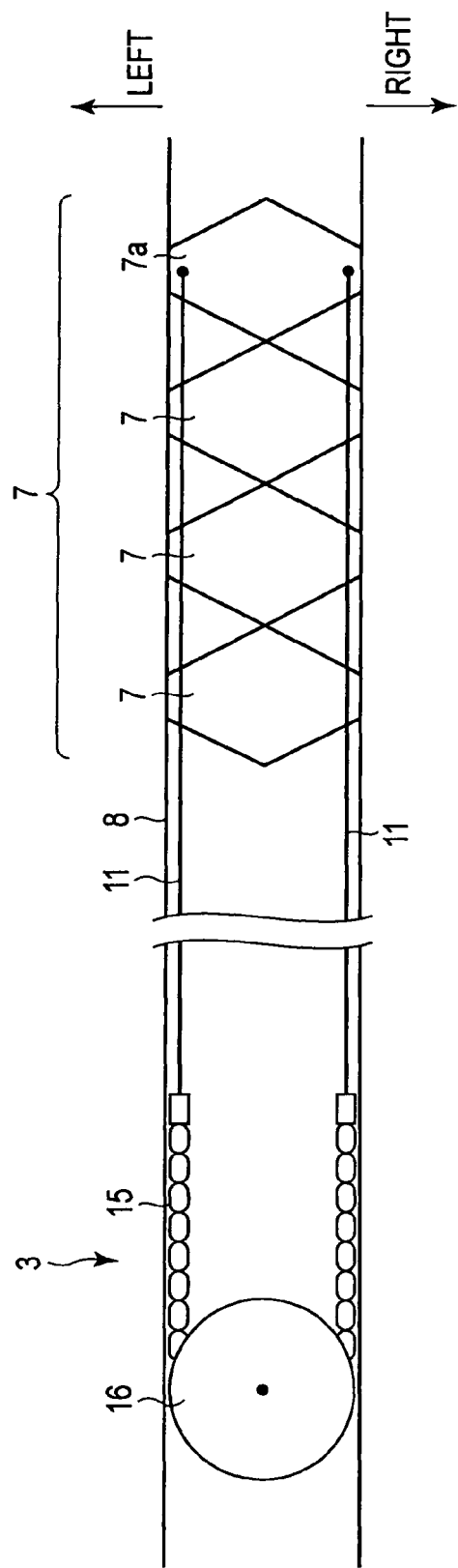
FIG. 3 is a diagram showing the configurations of the curving portion, the flexible tubular portion, and the endoscope device associated with a horizontal curving operation of the curving portion according to the first embodiment.

FIG. 2 and FIG. 3 are schematic diagrams showing the configurations of the curving portion 7, the flexible tubular portion 8, and the endoscope body 4 associated with curving operations of the curving portion 7.

Inside the curving portion 7, a string of metal joint rings 9 are linked in a longitudinal direction. More specifically, two joints are sequentially provided at opposite positions 90 degrees different from each other in a diametrical direction between the joint rings 9, and are substantially coaxially coupled rotatably relative to each other to produce a curving mechanism. These linked joint rings 9 are covered with a curving braid including cylindrically woven thin wires. The curving braid is further watertightly covered with a sheet member made of flexible fluorine-containing rubber. The flexible tubular portion 8 is a flexible long soft tube made of, for example, a fluorine resin.

The angle wires described later are coupled to each of the joint rings of the curving mechanism. Each angle wire is pulled to perform a curving operation between the joints. More specifically, in the curving portion 7, the distal end of an UD (up/down) angle wire 10 is coupled to a distalmost curving piece 9a at a position corresponding to the vertical direction of the curving portion 7, as shown in FIG. 2. Moreover, the distal ends of an RL (right/left) angle wire 11 are coupled to a distalmost curving piece 7a at a position corresponding to the horizontal direction of the curving portion 7, as shown in FIG. 3.

As shown in FIG. 2, the UD angle wire 10 extends into the endoscope body 4 from the distalmost curving piece 9a of the curving portion 7 through the flexible tubular portion 8 so that the proximal end of the UD angle wire 10 is wound around a rotary drum 12. A rotation shaft of a UD operation dial 14 for operating the vertical curving (angle) of the curving portion 7 is attached to a rotation shaft 13 of the rotary drum 12. Therefore, the curving portion 7 is curved upward or downward if the UD operation dial 14 is rotated.

As shown in FIG. 3, the RL angle wire 11 extends into the endoscope body 4 from the distalmost curving piece 9a of the curving portion 7 through the flexible tubular portion 8 so that the proximal end of the RL angle wire 11 is coupled to a chain 15 via a connection member. The chain 15 is wound around a sprocket 16, and the sprocket 16 is coupled to an RL curving drive portion 17.

Figure 4:
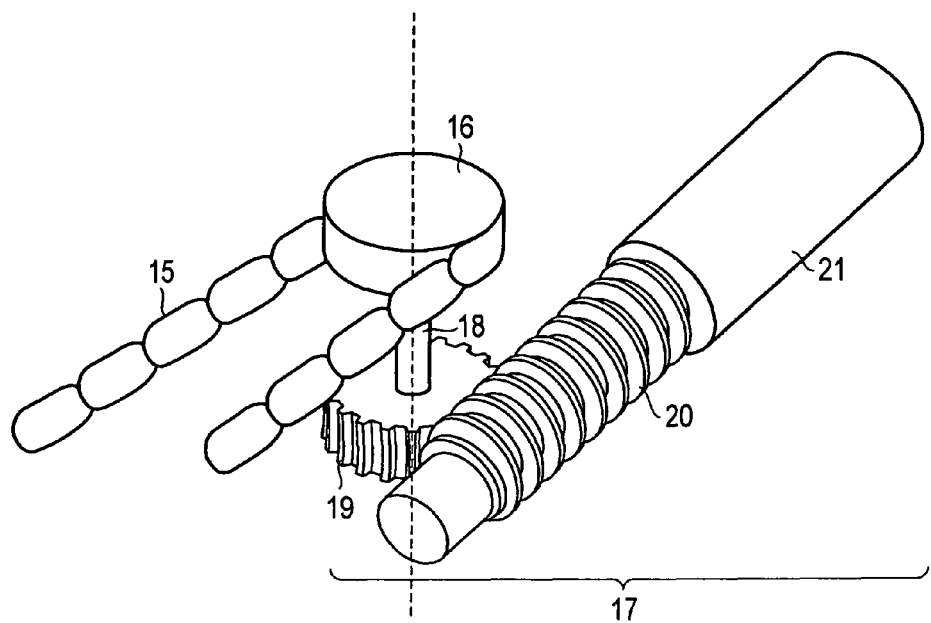
FIG. 4 is a schematic diagram showing a transmission structure of a drive mechanism for an RL curving operation inside an endoscope body.
Figure 5:
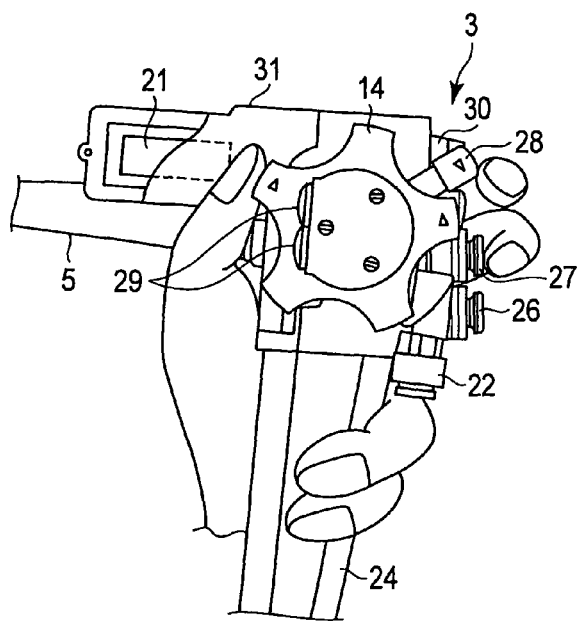
FIG. 5 is a diagram showing the endoscope body grasped by the hand of an operator and the inside of the endoscope body.

FIG. 4 is a schematic diagram showing a transmission structure of the RL curving drive portion 17 inside the endoscope body 4. FIG. 5 is a diagram showing the endoscope body 4 including a grasp portion 24 grasped by the hand of an operator and the operation portion 3, and also showing the inside of the endoscope body 4.

The RL curving drive portion 17 shown in FIG. 4 has a driving force transmission mechanism and an RL curving driving motor 21. The driving force transmission mechanism includes the sprocket 16 on which the chain 15 is put, a worm wheel 19 coaxially connected to the sprocket 16 by a shaft 18, and a worm gear 20 which is toothed with the worm wheel 19. The RL curving driving motor 21 is coupled to the worm gear 20.

Furthermore, a power cable of the motor 21 is connected to an unshown RL curving controller from the distal end of the electric cable inside the universal cord 5. An operation input unit (RL operation input unit) 22 for an RL operation to indicate a curving amount (curving angle) of the curving portion by a rotational operation is also connected to the RL curving controller by the universal cord 5. Although the input unit is described as the RL operation input unit in the present embodiment, the input unit can also be used as a UD operation unit as in the second embodiment.

When a curving operation signal indicating a horizontal curving operation input to the operation input unit 22 is output to the RL curving controller, the RL curving controller drives the motor 21 in accordance with the curving operation signal. The motor 21 then generates driving force to horizontally curve the curving portion 7, and the RL angle wire 11 is pulled via the driving force transmission mechanism. Thus, the curving portion 7 is electrically curved in one axial direction, that is, in the leftward or rightward direction in accordance with the curving direction of the rotational operation of the operation input unit 22 and the amount of this operation.

Regarding the operation of the curving portion 7 to insert the flexible tubular portion 8 into a twisting body cavity, the vertical curving operation is not equal to the horizontal curving operation. The vertical curving operation is the main operation, and the horizontal curving operation is often secondarily used, for example, during observation. Therefore, in the present embodiment, the vertical curving operation is performed by the manual operation mechanism, and the horizontal curving operation is electrically performed. It should be appreciated that the present invention is not limited and both the dials may be electric.

A support portion 23 which supports the proximal end of the flexible tubular portion 8 is provided on the distal side of the endoscope body 4. The distal end of the support portion 23 is tapered toward the proximal end of the flexible tubular portion 8. The grasp portion 24 which is grasped by the operator as shown in FIG. 5 is provided on the proximal side of the support portion 23. The grasp portion 24 is provided with a forceps insertion opening 25 which is in communication with the above-mentioned forceps channel formed in the insertion portion 2. A treatment tools such as an ultrasonic probe or a biopsy forceps is inserted into the forceps insertion opening 25 to treat a lesion in the body cavity.

The operation portion 3 for various operations of the endoscope device 1 including the curving operation of the curving portion 7 is provided on the proximal side of the grasp portion 24. Arranged in the operation portion 3 are the above-mentioned UD operation dial 14, the above-mentioned operation input unit 22, an air/water supply button 26, a suction button 27, a UD curving operation fixing lever 28, function switches 29 and 30, and a driving unit 31 containing a driving source such as a motor.

The UD operation dial 14 is rotatably provided on a first shaft protruding from one side of the operation portion 3. As shown in FIG. 5, the operator who is grasping the grasp portion 24 with one hand (left hand) puts the tip of the thumb of this hand to rotationally operate the UD operation dial 14. As a result, the above-mentioned UD angle wire 10 is operated, and the curving portion 7 then moves up or down. The UD curving operation fixing lever 28 is a brake which fixes the curving portion 7 at a desired angle.

The function switches 29 are disposed on the upper surface of the UD operation dial 14. For example, a function of obtaining an image of an observed part and a function of magnifying images are allocated to the function switches 29. The other function switches 30 to which, for example, a photometry switching function and an image fixing function are allocated are disposed on the side surface in which the air/water supply button 26 and the suction button 27 are provided.

As shown in FIG. 1 and FIG. 5, the operation input unit 22 is rotatably provided on a second shaft protruding in the longitudinal axis direction of the endoscope body 4 from the side closer to the grasp portion 24 than the position where the UD operation dial 14 is provided. That is, the operation input unit 22 is located under the air/water supply button 26 and the suction button 27 to have a rotation axis substantially parallel to the longitudinal axis direction of the grasp portion 24.

The operation input unit 22 is also rotated when the operator who is holding the grasp portion 24 with one hand uses, for example, the middle finger other than the thumb of this hand to perform an operation input in a direction crossing the longitudinal axis of the grasp portion 24 substantially at right angles. That is, the operation input unit 22 is located within a range in which the operation input unit 22 can be operated by the middle finger other than the thumb of one hand of the operator who is holding the grasp portion 24 with this hand. The above-mentioned motor 21 for RL curving driving and the motor housing portion 31 containing this motor 21 are located along the universal cord 5 which substantially perpendicularly extends from the longitudinally extending endoscope body 4.

Figure 7:
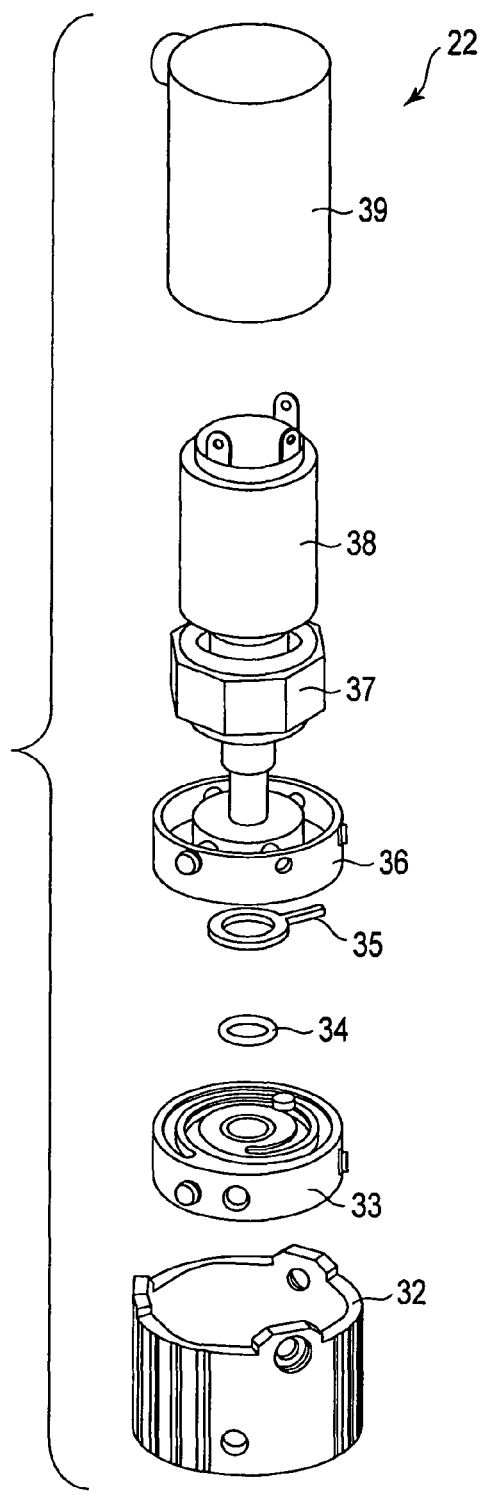
FIG. 7 is an exploded perspective view of the RL operation input unit.
Figure 8:
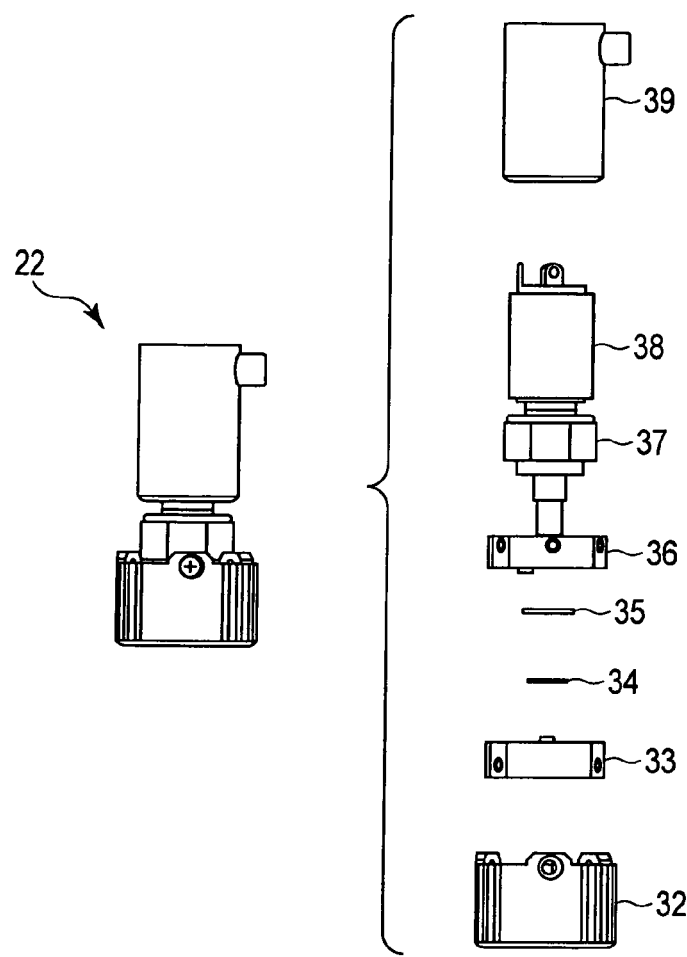
FIG. 8 shows a front view and an exploded view of the RL operation input unit.

FIG. 6 is a perspective view showing the overall external configuration of the operation input unit 22 for the RL operation according to the present embodiment. FIG. 7 is an exploded perspective view of the operation input unit 22. FIG. 8 shows a front view and an exploded view of the RL operation input unit 22.

As shown in FIG. 7, the operation input unit 22 has an operation dial 32, a CCW lead unit 33, a washer 34, a lever 35, a CW lead unit 36, a fixing screw 37, a potentiometer 38, and a rubber cover 39. These components are combined to constitute the operation input unit 22.

The operation dial 32 is a cylindrical cover member. The CCW lead unit 33, the washer 34, the lever 35, and the CW lead unit 36 are housed in the operation dial 32. The operation dial 32 housing these components is diametrically rotatably attached to the fixing screw 37. Further, the fixing screw 37 is coupled to the potentiometer 38 having its outer circumferential surface covered with the rubber cover 39. When the operator rotationally operates the operation dial 32, the angle of this rotation is detected by the potentiometer 38, and a curving operation signal is then input to the unshown RL curving controller, as described above. For example, a rotary hall sensor may be used instead of the potentiometer 38.

Figure 9:
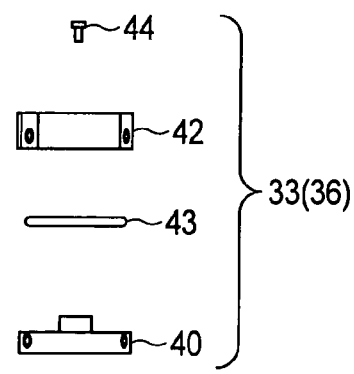
FIG. 9 is an exploded view of a CCW lead unit.
Figure 10:
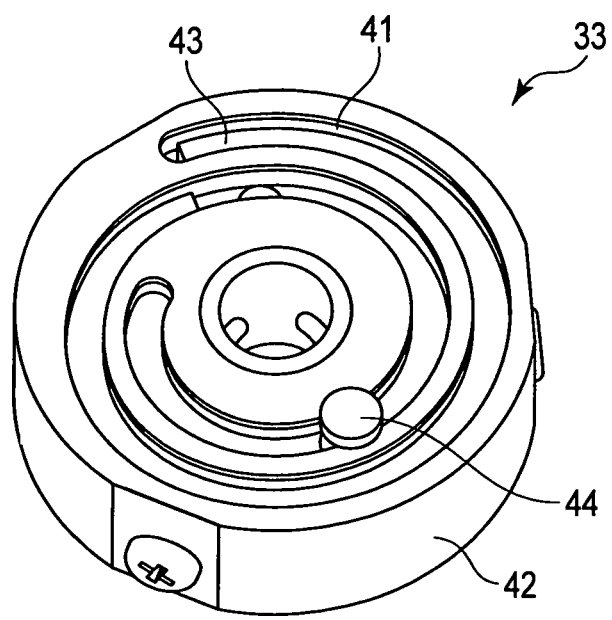
FIG. 10 is a perspective view of the CCW lead unit.

FIG. 9 is an exploded view of the CCW lead unit 33. FIG. 10 is a perspective view of the CCW lead unit 33.

The CCW lead unit 33 has a lower CCW fixed plate 40, an upper CCW lead plate 42, a spring 43 as an elastic member, and a pin 44. Among these components, the CCW lead plate 42 is a frame material in which a spiral groove 41 is formed in a CCW direction. The spring 43 is attached to and housed in one end in the groove 41, and acts as the elastic member to be set into a predetermined range inside the groove 41. The pin 44 is an abutting portion which slides along the groove 41 and abuts on the spring 43.

Moreover, the lower CCW fixed plate 40 and the CCW lead plate 42 are screwed in their outer circumferential surfaces and thus set so that the upper CCW lead plate 42 covers the lower CCW fixed plate 40.

The CW lead unit 36 has the same configuration as the CCW lead unit 33. That is, the CW lead unit 36 has a lower CCW fixed plate 45, an upper CCW lead plate 47 in which a spiral groove 46 is formed in a CW direction, a spring 48 set in the groove 46, and a pin 49 as an abutting portion which slides over the groove 46 and abuts on the spring 48.

The lever 35 as an action portion which applies force to the pin 44 and the pin 49 is located between the CCW lead unit 33 and the CW lead unit 36 via the washer 34. As shown in FIG. 7, the lever 35 has a ring shape with a diametrically extending portion. The lever 35 is disposed to be able to contact with both the lower pin 44 and the upper pin 49. When the operator has rotated the operation dial 32, the lever 35 contact with the lower pin 44 or the upper pin 49, and the pin 44 and the pin 49 then contact with the spring 43 or the spring 48, so that the spring 43 or the spring 48 is compressed.

The operations of the CCW lead unit 33 and the CW lead unit 36 are described here. FIG. 11A and FIG. 11B are schematic views showing return mechanisms of the CCW lead unit 33 and the CW lead unit 36. The spiral grooves 41 and 46 of the CCW lead unit 33 and the CW lead unit 36 are shown in a linear form in these drawings.

The spring 43 and the pin 44 of the CCW lead unit 33 and the spring 48 and the pin 49 of the CW lead unit 36 are vertically separately located symmetrically with respect to the lever 35.

As shown in FIG. 11A, a length region in which the spring 43 of the CCW lead unit 33 has a natural length is a region A, a length region in which the spring 48 of the CW lead unit 36 has a natural length is a region C, and a region between the region A and the region C is a region B. The neutral positions of the operation dial 32 and the lever 35 are located in the center of the region B.

Here, the region A is the range in which the elastic force of the spring 48 is effective, and the region C is the range in which the elastic force of the spring 43 is effective. The region B is a range in which the elastic forces of the springs 43 and 48 are not effective. A range L of the region B is set by a positional relation between the neutral position and the lever 35 when the springs 43 and 48 have the natural lengths. For example, if the neutral position is located apart from the lever 35 when the springs 43 and 48 have the natural lengths, a desired curving state of the curving portion 7 can be included in this range. If the neutral position is not located apart from the lever 35 when the springs 43 and 48 have the natural lengths, the operation dial 32 and the lever 35 always return to the neutral positions so that the curving portion 7 can be returned to an uncurved state. When the operation dial 32 and the lever 35 are located at the neutral positions, the curving portion 7 has a horizontal curving angle of 0°, that is, is not horizontally curved.

If the operation dial 32 is rotated in the CCW direction by the hand of the operator so that the lever 35 is moved to the region A, the lever 35 presses the pin 44 to compress the spring 43. As a result, the curving portion 7 is, for example, curved leftward. If the rotational operation input to the operation dial 32 is then stopped and the hand is taken off the operation dial 32, the lever 35 is pressed back by the elastic force (urging force) of the spring 43, and then returns to the predetermined region B which is a rotation range where the neutral position is included and the position of the operation dial 32 is maintained and in which the elastic force of the spring 43 is not effective. That is, the spring 48, the lever 35, and the pin 44 function as a return force generating portion which generates return force to return the operation dial 32 to the neutral position. Here, the return force is force to return the operation dial 32 to a preset range or rotation angle including the neutral position. As a result, the curving portion 7 returns to a leftward curving state (including a linear state) within a preset angle range (region B).

On the other hand, if the operation dial 32 is rotated in the CW direction by the hand of the operator so that the lever 35 is moved to the region A, the lever 35 presses the pin 49 to compress the spring 48. As a result, the curving portion 7 is, for example, curved rightward. If the rotational operation input to the operation dial 32 is then stopped and the hand is taken off the operation dial 32, the lever 35 is pressed back by the elastic force of the spring 48, and then returns to the region B in which the elastic force of the spring 48 is not effective. The region B is a predetermined rotation range which includes the neutral position and in which the position of the operation dial 32 is maintained. As a result, the curving portion 7 returns to a rightward curving state (including a linear state) within a preset angle range (region B). That is, the spring 48, the lever 35, and the pin 49 function as a return force generating portion which generates return force to return the operation dial 32 to the neutral position. Here, the return force is force to return the operation dial 32 to a preset range or rotation angle including the neutral position.

Figure 12A:
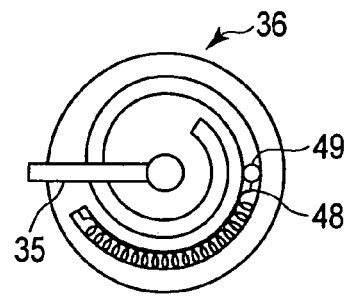
FIG. 12A is an upper view showing a return mechanism of the CW lead unit.
Figure 12B:
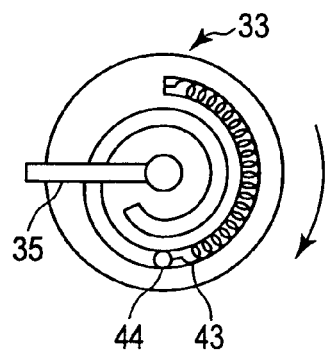
FIG. 12B is an upper view showing a return mechanism of the CCW lead unit.

FIG. 12A and FIG. 12B are upper views showing the actual state of the above-mentioned return mechanisms in the CCW lead unit 33 and the CW lead unit 36. If the operation dial 32 is rotated clockwise, the lever 35 is also rotated clockwise and then abuts on the pin 49. If the hand is taken off the operation dial 32 so that the lever 35 compresses the spring 48 via the pin 49, the lever 35 is returned counterclockwise, and then returned to the range in which the elastic force from the spring 48 is not effective.

If the operation dial 32 is rotated counterclockwise, the lever 35 is also rotated counterclockwise and then abuts on the pin 44. If the hand is taken off the operation dial 32 so that the lever 35 compresses the spring 43 via the pin 44, the lever 35 is returned clockwise, and then returned to the range (state B) in which the elastic force from the spring 43 is not effective.

Thus, when the lever 35 is moved to the regions A and C beyond the preset rotation angle and rotation number of the operation dial 32, the lever 35 is returned to the region B including the neutral position by the elastic forces of the springs 43 and 48 if the operator takes the hand off the operation dial 32, and the lever 35 maintains the curving state (including a linear state) at the time. If the operation dial 32 is at the rotation angle and the rotation number such that the lever 35 is not beyond the region B, the elastic forces of the springs 43 and 48 are not effective, and the lever 35 maintains the curving state (including a linear state) of the curving portion at the time.

According to the present embodiment, in the electrically curved endoscope device in which the curving portion is curved and driven by the motor, the horizontal curving operation in the curving portion is electric, and a small rotary operation dial is used so that the curving operation can be manipulated by one hand grasping the endoscope device. In such an endoscope device, operational sensitivity is preferably higher for improved operability. Thus, the rotation amount of the operation dial is more than one rotation for the curving angle. That is, the ratio of the rotation amount of the operation dial to the curving angle is preferably higher (e.g. a curving angle 1 of the insertion portion: an operation angle 3 of the operation dial). However, in the case of the multiple rotations of the operation dial, the operator cannot easily sense the curving amount of the curving portion from the state of the operation dial, and the operation tends to be unstable.

According to the present embodiment, the RL operation dial which is a curving operation input portion is a small multiple-rotation operator operable with one hand. However, if the operator takes the hand off the RL operation dial, the curving portion returns to a predetermined curving state toward the neutral position even when the curving portion is curved either leftward or rightward. Therefore, the operator can operate without hesitation.

When the curving portion should be returned to the neutral position, it is difficult to determine the neutral position in the case of the multiple-rotation operation dial. Moreover, in the curving operation, at a certain curving angle, an engage function works to lock the curving portion at a given curving angle. When a neutral return mechanism should be used at an angle equal to or more than a certain degree, a mechanism including both a mechanism for return to the neutral position and an engage mechanism is not easily reduced in size or is lower in operability.

According to the present embodiment, the RL operation dial can be set to return to a predetermined range of curving angle from 0° without completely returning to the neutral position (i.e. a curving angles of 0°). This curving angle range can be set to, for example, ±75° or ±90°. This is because in this range, the operation dial generally does not need to return to the neutral position from an operational perspective and because the insertion into or treatment of the body cavity is rather easier when the engage function works to lock the curving portion at a given curving angle.

Thus, in the present embodiment, the RL operation dial functions as the return mechanism to return the curving portion to the uncurved state or as the engage function to lock the curving portion in a desired curving state. Consequently, it is possible to provide an endoscope device which can easily return the curving angle of the curving portion to a desired range even if a multiple-rotation operation is input.

Figure 13:
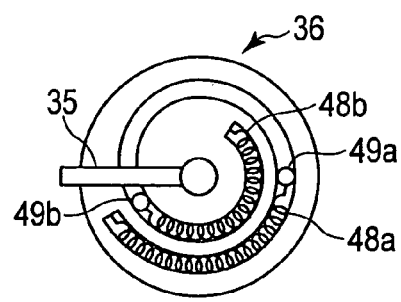
FIG. 13 is an upper view showing a return mechanism of a CW lead unit according to a modification.

FIG. 13 is an upper view showing the return mechanism of the CW lead unit 36 according to a modification of the present embodiment. In this modification, springs 48a and 48b are respectively set in predetermined ranges of the groove 46 from both ends of the groove 46 of the CW lead unit 36. Pins 49a and 49b which slide over the groove 46 and which respectively abut on the springs 48a and 48b are provided in the groove 46.

In such a configuration as well, the lever 35 can return to a range in which forces from the springs 48a and 48b are not effective in both rotation directions.

Second Embodiment

Now, an endoscope device according to the second embodiment is described.

FIG. 14 is a block diagram showing the general configuration of the endoscope device according to the second embodiment. Components according to the present embodiment equivalent to those in the first embodiment described above are provided with the same reference signs and are not described in detail.

A connector is used to removably connect an endoscope body 4 to devices mounted on a trolley 58 through a universal cord 56 including, for example, a light guide and an electric cable. The devices used include at least a light source device which guides illumination light, a video processor device which converts an image obtained by the endoscope body 4 to a display image signal, and a monitor 57 which displays an image resulting from the image signal output by the video processor device.

According to the present embodiment, operation input units 22 are provided in both an RL operation dial 55 and a UD operation dial 14 for electric operation. The configuration of an operation portion 3 is equivalent to the configuration shown in FIG. 5. The configuration of an RL curving drive portion 17 is equivalent to the configuration shown in FIG. 4. A sensor 57 is provided to detect the rotation amounts (positions) of pulleys 54a and 54b.

Motors 53a and 53b are connected to an unshown RL curving controller from the distal end of an electric cable inside a universal cord 5. The operation input units 22 are also connected to the RL curving controller by the universal cord 5.

When a curving operation signal indicating a horizontal curving operation input to the RL operation input units 22 is output to the RL curving controller, the RL curving controller drives the motor 53b in accordance with the curving operation signal. The motor 53b then generates driving force to horizontally curve a curving portion 7, and an RL angle wire 11b is pulled via a driving force transmission mechanism. Thus, the curving portion 7 is electrically curved in one axial direction, that is, in the leftward or rightward direction in accordance with the curving direction of the rotational operation of the operation input unit 22 and the amount of this operation.

When a curving operation signal indicating a vertical curving operation input to the RL operation input units 22 provided in the UD operation dial 14 is output to a UD curving controller, the UD curving controller drives the motor 53a in accordance with the curving operation signal. The motor 53a then generates driving force to vertically curve the curving portion 7, and a UD angle wire 11a is pulled via the driving force transmission mechanism. Thus, the curving portion 7 is electrically curved in one axial direction, that is, in the leftward or rightward direction in accordance with the curving direction of the rotational operation of the operation input unit 22 and the amount of this operation.

Modification of Second Embodiment

Now, a first modification of the operation dial of the endoscope body according to the second embodiment is described. In an example of the operation portion 3 shown in FIG. 15A, a starlike UD operation dial 14 is provided on the side surface of the operation portion 3, and a cylindrical RL operation dial 55 for horizontal curving is attached to the center of the upper surface of the UD operation dial 14. This operation dial 55 corresponds to a dial cover 73 of the operation input unit 22, and is attached to the housing of the operation portion 3 so that a potentiometer 62 is housed in the housing.

In another example of the operation portion 3 shown in FIG. 15B, the UD operation dial 14 is attached to the side of the housing of the operation portion; and the operation dial 55 (operation input unit 22) smaller than the UD operation dial 14 is disposed on the same rotation axis over the UD operation dial 14.

FIG. 16 shows the external configuration of an operation input unit 61. FIG. 17 is a diagram showing the internal configuration of the operation input unit 61 without a case. FIG. 18 is a diagram showing the assembly configuration of the operation input unit 61.

The operation input unit 61 has such a technical characteristic as to return a dial portion 63 which is an operation portion to a predetermined neutral position (initial position) when an accumulated rotational operation of the dial portion 63 has exceeded a predetermined rotation angle range. The predetermined neutral position referred to here suggests an initial position in which the curving portion 7 is substantially linearly extended.

The operation input unit 61 comprises the potentiometer 62 and the dial portion (dial position returning portion) 63. The potentiometer 62 has a known configuration, and is a part which indicates the position (rotation angle) of an output shaft 64 by a voltage change. For example, when a reference voltage is being applied to a fixed electrode (e.g. fixed resistance portion), an output value linearly changes in response to the position where a movable electrode provided in the output shaft is in contact with the fixed electrode, that is, in response to the rotation angle of the output shaft. Therefore, if an output voltage is previously related with the angle, the rotation angle of the output shaft can be calculated from an output voltage value. Two terminals 62a connected to the fixed electrode, and one terminal 62a connected to the movable electrode are provided at the rear end of the potentiometer 62.

The dial portion 63 comprises a return force generating portion and a rotation resistance generating portion. The return force generating portion has an ST nut 66, a coil spring 69 (69a, 69b) which is an elastic member, a spring plate 68, a D-plate 71, coil hook plates 70, the dial cover 73, and screws 74 which fix the above components.

More specifically, the ST nut 66 is a member to attach the endoscope operation portion 3 to the housing. The ST nut 66 has a cylindrical shape having a through-hole formed in the center to rotatably pass the output shaft 64 of the potentiometer 62. The cylindrical upper side of the ST nut 66 has a cap shape with a collar, and a diametrically large portion above the collar is polygonal, for example, hexagonal or octagonal. An annular groove is formed in the inner surface of the through-hole. An O-ring 67 made of an elastic member having a high frictional coefficient (sliding resistance) such as a rubber material to be the rotation resistance generating portion is fitted in the annular groove. The depth of this groove is adjusted and formed so that about half of the diameter of the thickness φ of the O-ring 67 is exposed when the O-ring 67 is fitted in.

The spring plate 68 is screwed to the lower part of the ST nut 66. The D-plate 71 is then rotatably set to the lower part of the ST nut 66, and the coil hook plates 70 are put on and screwed to the lower parts of both sides of the D-plate 71. Screw receivers 72a and 72b are provided in the bottom surface of the D-plate 71.

A hole (bottomed hole) into which the output shaft 64 of the potentiometer 62 is fitted is formed in the center of the D-plate 71, and a cave hole is laterally formed in the vicinity of the bottom. This cave hole is formed to couple the fitted output shaft 64 to the D-plate 71. For example, a screw 65 such as a hexagon socket head screw is screwed into a screw hole formed in the distal side part of the output shaft 64 through the cave hole, and the output shaft 64 and the D-plate 71 are thereby engaged.

Hook portions respectively protrude in the spring plate 68 and the coil hook plates 70. Both ends of the metallic coil spring 69 (69*a*, 69*b*) are hooked between the hook portions. In the configuration of this example, two coil springs 69*a* and 69*b* are used to generate return force described later. However, it should be appreciated that the number of coil springs used is not limited. A configuration that uses one coil spring may be provided, or a configuration that uses three or more coil springs may be provided.

During assembly, the potentiometer 62 is fixed to the collar of the ST nut 66. About half of the external part of the O-ring 67 fitted in the groove is exposed. When covered with the dial cover 73, this part of the O-ring 67 is pressed by the inner surface of the cover and slightly deformed. This deformed part serves as the rotation resistance generating portion to generate locking force (engagement), that is, rotation resistance force against the rotation resulting from the sliding resistance. The inner surface of the cover to contact the O-ring 67 may be formed or treated to have a rough surface so that the sliding resistance may be increased. This includes, for example, blasting or the formation of a groove pattern (e.g. multiple parallel grooves in a direction that crosses the sliding direction of the O-ring 67 at right angles.

Furthermore, the D-plate 71 is fixed to the dial cover 73 and the screws 74. The D-plate 71, the output shaft 64, and the dial cover 73 are linked together, and are rotatable relative to the ST nut 66.

The operation input unit 22 having such a configuration is mounted by fitting and fixing the ST nut into a mounting hole made in the housing of the operation portion 3 to expose the dial portion 63 so that the potentiometer 62 is housed in the housing. When attached to the housing, the ST nut 66 is watertightly fixed via, for example, a packing. The dial cover 73 may be the operation dial 55, as shown in FIG. 15B.

Now, the operation of the dial portion 63 in the operation input unit 61 fixed to the housing of the operation portion 3 is described.

The holding position of the dial portion 63 rotated by the operator can be defined by a neutral return characteristic described below which is set by the adjustment of, for example, the elastic force of the coil spring described later and the pressure (sliding resistance force or frictional coefficient) of the O-ring 67 against the inner surface of the cover.

The neutral return characteristic resulting from the combination of the rotation resistance (sliding resistance) characteristic of the O-ring 67 and the spring characteristic (rotation torque characteristic) of the coil spring 69 is described with reference to FIG. 19. Here, the horizontal axis indicates the rotation angle of the rotated dial portion 63 and an angle rotation angle of the curving state (i.e. curving angle) of the curving portion relative to the rotation angle, while the vertical axis indicates the rotation torque applied to the dial portion 63.

In the present embodiment, force which returns the dial portion 63 to a set range or rotation angle including the initial position (neutral position) is referred to as the return force. This return force is mainly the elastic force of the elastic member, in the present embodiment, the coil spring. In addition, the return force may slightly include force resulting from the tube covering the curving mechanism, and force against the spread of the angle wire. In the present embodiment, these forces are not taken into consideration. Although the spring that uses elasticity attributed to the extension and contraction is used in the present embodiment, it is also possible to use an elastic member that uses elasticity attributed to twisting.

The dial portion 63 is rotated in both the clockwise (CW) direction and the counterclockwise (CCW) direction around the neutral position (zero degrees). When the dial portion 63 is rotated in a rotation range with a maximum rotation angle of ±540 degrees, an angle rotation angle θ of the curving portion is set to ±160 degrees at the maximum. The maximum rotation angle of the dial portion 63 and the curving angle (angle rotation angle) of the curving portion are design matters, and are properly set angles.

The neutral return characteristic according to the present embodiment is described.

Figure 19:
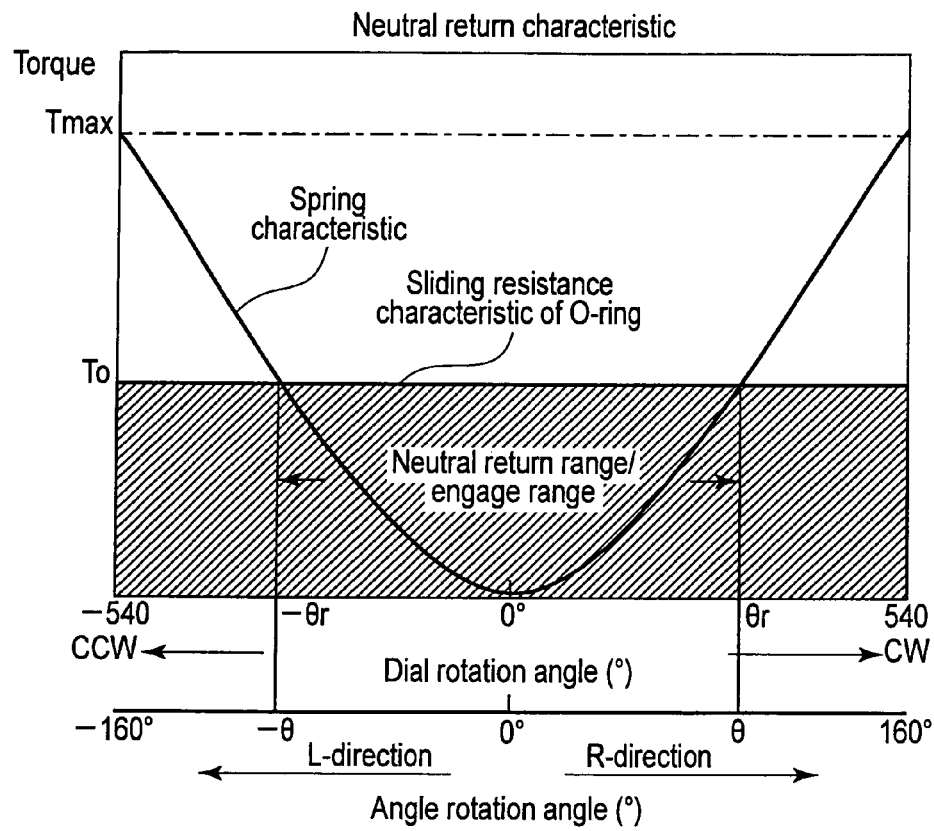
FIG. 19 is a graph showing a neutral return characteristic.

The spring characteristic shown in FIG. 19 corresponds to the elastic force generated by the coil spring 69 which is the elastic member used in the present embodiment, and acts on the dial portion 63. This spring characteristic has a linear V-shape in which rotation torque T at the neutral position of the dial portion 63 is 0 (or in the vicinity of 0) and rotation torque T at the maximum angle is ±Tmax. Rotation resistance force $T_0$ is indicated as the sliding resistance characteristic of the O-ring 67, and more specifically, is sliding resistance between the O-ring 67 and the cover inner surface and has a constant value.

In FIG. 19, the position where the rotation torque (spring characteristic) T crosses the rotation resistance force $T_0$ as a standard is a dial rotation angle ±θr of the dial portion 63, and a rotation angle range of −θr to θr is an engage range in which the position of the dial portion 63 is maintained.

That is, if the rotation torque T is less than the standard rotation resistance force $T_0$ as the standard, the rotation resistance force surpasses, and the ST nut and the dial cover 73 (rotation shaft 4) are held at the position (rotation angle) without sliding. That is, the curving state of the curving portion 7 is maintained even if the operator takes the hand off the dial portion 63 (operation dial).

In contrast, as an angle rotation angle ±θ of the curving portion 7 at the dial rotation angle ±θr, a rotation angle range corresponding to −Tmax to −θr and θr to Tmax is a neutral return range (engage free range).

When the operator rotates the dial portion 63 to increase a rotation angle more than ±θr, the rotation torque T exceeds the level of the elastic force $T_0$. In this case, if the operator takes the hand off the dial portion 63 (or the operation dial), slippage is caused between the O-ring 67 and the cover inner surface. As a result, the dial portion 63 (rotation shaft 4) is restored to the engage range including the neutral position determined by the elastic force of the coil spring 69, that is, the curving portion 7 is returned to the preset relatively extended curving state.

In the present embodiment, the engage range is set into a rotation angle of ±90 degrees around the neutral position. This engage range is set on the ground of the curving state of the curving portion which makes it easy to approach an observation target to be treated and observed. It should be appreciated that a return position can be freely set and can be set to the neutral position (initial position) or a position located in its vicinity.

As described above, the endoscope device according to the present embodiment enables the size reduction of the operation portion and allows the operation portion to be electrically operated, and can therefore be grasped and operated by one hand of the operator. Since this operation input unit 61 is mounted in the endoscope device, the exposed members are made of materials that can resist, for example, sterilization washing, and have watertight structures.

The engage range is set in the dial portion and the operation dial. At a rotation angle within this engage range, the position at this rotation angle is maintained even if the operator temporarily takes the hand off the dial portion or the operation dial. Therefore, the curving state of the curving portion is maintained, and the target part which has been observed does not come out of the observation field and can be kept observed.

When the operator repeats the rotational operation of the operation portion leftward and rightward, it has been impossible for the operator to recognize the current curving angle of the curving portion in a displayed observation image. Accordingly, the operation input unit is applied to the operation portion of the endoscope device so that when the hand is taken off, the operation dial or the dial portion which has been rotationally operated to the set neutral return range is returned to the position within the engage range set by the elastic force resulting from the coil spring and the sliding resistance force resulting from the O-ring. As a result, when the curving state cannot be recognized, the operation dial or the dial portion is returned to the curving state within a predetermined range including the neutral position if rotated to the neutral return range. Therefore, the operator can perform the curving operation without feeling insecure in the process of the operation or without hesitating whether to return the operation dial or the dial portion to the neutral position.

Third Embodiment

Figure 20:
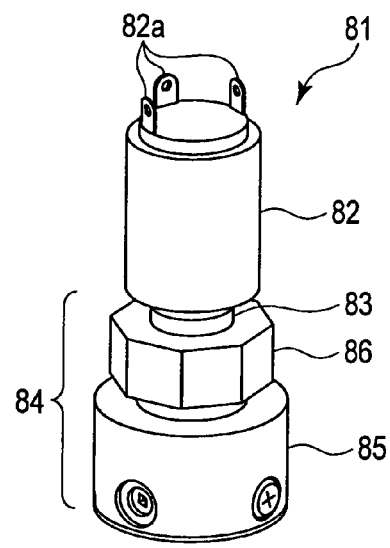
FIG. 20 is a diagram showing the external configuration of an operation input unit of an endoscope body according to a third embodiment.
Figure 21:
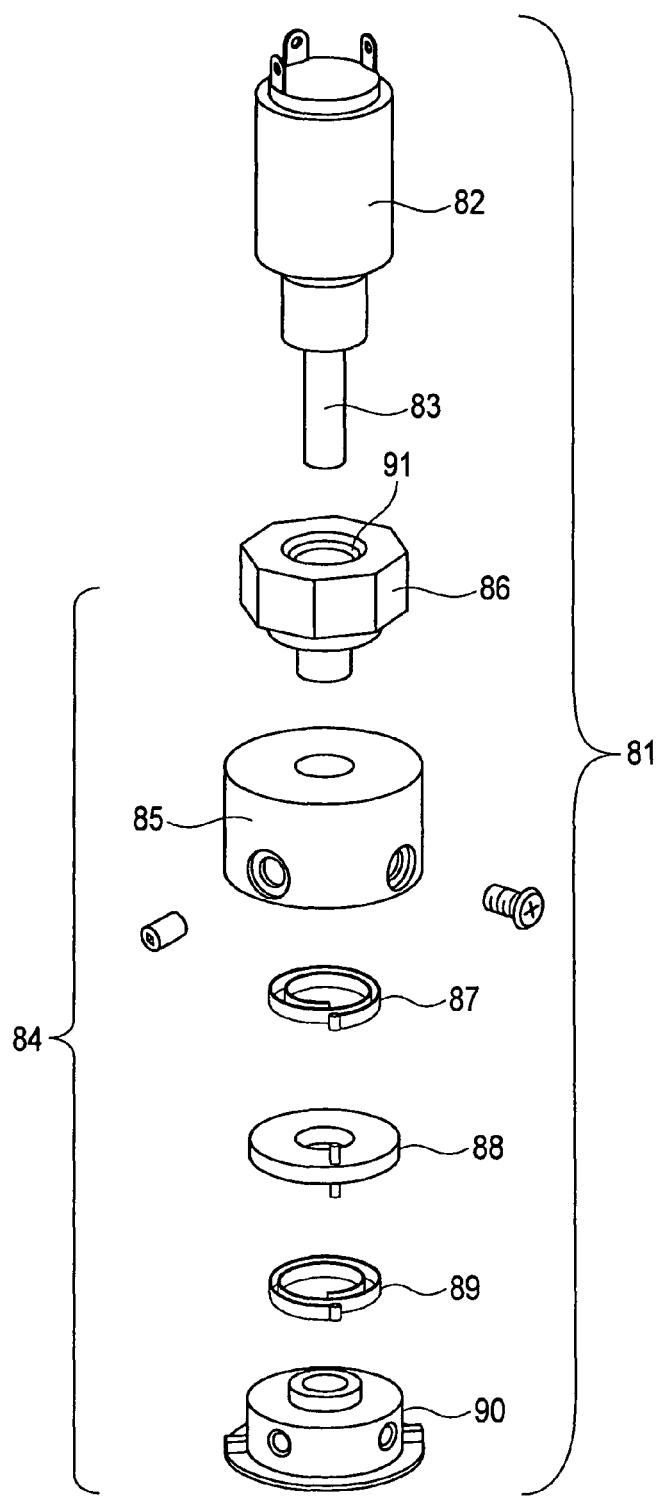
FIG. 21 is a diagram showing the assembly configuration of the operation input unit.

FIG. 20 shows the external configuration of an operation input unit of an endoscope body according to the third embodiment. FIG. 21 is a diagram showing the assembly configuration of an operation input unit 81.

The operation input unit 81 according to the present embodiment is configured to use elastic force resulting from two spiral springs 87 and 89 instead of the above-mentioned coil spring as torque applied to a dial portion 63.

As shown in FIG. 20, the operation input unit 81 comprises a potentiometer 82 and a dial portion 84. The potentiometer 82 has a configuration equivalent to that of the potentiometer 62 described above. The potentiometer 82 is provided with two terminals 82a connected to a fixed electrode, and one terminal 82a connected to a movable electrode. Detailed explanations are not given here.

The dial portion 84 comprises a return force generating portion and a rotation resistance generating portion, as in the first embodiment.

The return force generating portion comprises an attachment nut 86, a cylindrical cap 85, a spiral spring 87 wound in the CCW direction, a fixed plate 88 which couples springs, a spiral spring 89 wound in the CW direction, and a rotary plate 90 which is fitted in and fixed to the cylindrical cap 85.

The attachment nut 86 has a polygonal outer shape, for example, a octagonal outer shape, and has a protruding sectional shape. Further, a through-hole is formed in the center of the nut to fit an output shaft 83 of the potentiometer 82 and pass the output shaft 83. An annular groove is formed in the inner circumferential surface of the through-hole, and an O-ring 91 is fitted in the groove. The depth of this groove is adjusted and formed so that about half of the diameter of the thickness φ of the O-ring 91 is exposed when the O-ring 91 is fitted in.

The exposed outer part of the O-ring 91 is pressed by the output shaft 83 and slightly deformed. This deformed part serves as a rotation resistance generating portion to generate locking force (engagement), that is, rotation resistance force against the rotation resulting from sliding resistance.

The cylindrical cap 85 also has a function of a operation dial, and houses the spiral spring 87, the fixed plate 88, and the spiral spring 89 that are set as described later. The rotary plate 90 is put on and screwed to the cylindrical cap 85.

The fixed plate 88 is housed in the cylindrical cap 85, and has a disk shape with a diameter that separates the spiral springs 87 and 89. A through-hole to pass the output shaft 83 is formed in the center of the fixed plate 88. Moreover, fixing pins are erected on the outer circumferential sides of both surfaces of the fixed plate 88. Fixing pipes provided in the outer circumferential ends of the spiral springs 87 and 89 are fitted in the pins. The fixed plate 88 functions as a hub for the spiral springs 87 and 89 located on both sides.

A hole (bottomed hole) into which the output shaft 83 is fitted is formed in the center of the rotary plate 90, and a cave hole is laterally formed in the vicinity of the bottom. As in the second embodiment described above, a hexagon socket head screw, for example, is screwed into a screw hole formed in the distal side part of the output shaft 83 through the cave hole, and the output shaft 83 and the rotary plate 90 are thereby engaged.

Now, how to set the spiral springs 87 and 89 to the cylindrical cap 85 and the fixed plate 88 is described with reference to FIG. 22. Here, the fixed plate 88 is not shown in FIG. 22. First, the spiral spring 87 is fitted into an unshown annular protrusion (which is the same as what is provided in the rotary plate 90) provided in the center of the cylindrical cap 85, and the inner end of the spiral spring 87 is fixedly connected to the annular protrusion.

The spiral spring 87 is then wound up in the CW direction several times (varying according to the degree of the spring constant), and the fixing pipe is fitted into the fixing pin of the fixed plate 88, so that the spiral spring 87 is kept wound up. Further, the spiral spring 89 is fitted into the annular protrusion provided in the center of the fixed plate 88 to fixedly connect the other end of the spring, and the spiral spring 89 is wound up in the CCW direction the same time as the spiral spring 87, and then fitted into the fixing pin on the opposite side of the fixed plate 88 in a similar manner. As a result of this construction, the return force generating portion is produced. Moreover, the attachment nut 86 is mounted and set on the cylindrical cap 85, and the output shaft 83 of the potentiometer 82 is inserted into the through-hole of the attachment nut 86. As described above, a hexagon socket head screw, for example, is screwed into the cave hole of the rotary plate 90, and the output shaft 83 and the rotary plate 90 are thereby engaged.

The neutral return characteristic according to the present embodiment is described with reference to FIG. 23.

FIG. 23 shows the spring characteristic of the operation input unit, the engage range by a rotation resistance characteristic, and a neutral return range. Here, the horizontal axis indicates the rotation angle of the rotated cylindrical cap 85, and an angle rotation angle of the curving state of the curving portion relative to the rotation angle, while the vertical axis indicates the rotation torque applied to the cylindrical cap 85.

According to the present embodiment, when the cylindrical cap 85 is rotated in a rotation range with a maximum rotation angle of ±540 degrees, an angle rotation angle θ of the curving portion is set to ±160 degrees at the maximum, as in the second embodiment. The maximum rotation angle of the cylindrical cap 85 and the angle rotation angle of the curving portion are design matters, and are properly set angles.

This spring characteristic includes a CW characteristic and a CCW characteristic showing the elastic forces of the two spiral springs 87 and 89 different in winding direction in line symmetry with respect to the neutral position (zero degrees). Rotation torque at the neutral position in the cylindrical cap 85 is Tc, rotation torque T at the maximum angle of each of the spiral springs 87 and 89 is ±Tmax, and rotation torque T at the minimum angle is Tmin. The used part of this spring characteristic has a linear V-shape. Rotation resistance force $T_0$ is indicated as the sliding resistance characteristic of the O-ring 91, and more specifically, is sliding resistance between the O-ring 91 and the output shaft 83 and has a constant value.

The rotation resistance force $T_0$ is a standard, so that the position where the CW characteristic and the rotation torque T cross is a rotation angle −θr of the cylindrical cap 85, and the position where the CCW characteristic and the rotation torque T cross is a rotation angle θr. A rotation angle range of −θr to θr is an engage range in which the position of the cylindrical cap 85 is maintained. A rotation angle range corresponding to −Tmax to −θr and θr to Tmax is a neutral return range.

In the engage range, if the rotation torque T is less than the standard rotation resistance force $T_0$, the rotation resistance force surpasses, and the position (rotation shaft) of the cylindrical cap 85 is held without slippage between the O-ring 91 and the output shaft 83. That is, the curving state of the curving portion 7 is maintained even if the operator takes the hand off the cylindrical cap 85 (or the operation dial).

In the neutral return range, when the operator rotates the cylindrical cap 85 to increase a rotation angle more than ±θr, the rotation torque T exceeds the level of the elastic force $T_0$. In this case, if the operator takes the hand off the cylindrical cap 85 (or the operation dial), slippage is caused between the O-ring 91 and the output shaft 83. As a result, the cylindrical cap 85 is restored to the engage range, that is, the curving portion 7 is returned to the preset relatively extended curving state.

In the present embodiment, the engage range is set into a rotation angle of ±90 degrees around the neutral position, for the same reasons as those in the second embodiment. It should be appreciated that a return position can be freely set and can be set to the neutral position (initial position) or a position located in its vicinity.

As described above, according to the present embodiment, advantageous effects equivalent to those in the second embodiment described above can be obtained. The operation input unit according to the present embodiment uses the spiral spring. Therefore, a further size reduction is possible. A rotation number of the cylindrical cap (operation dial) larger than that of the coil spring can be set. A small angle change can be made in the curving portion.

Fourth Embodiment

FIG. 24 is a diagram showing a conceptual configuration of an electrically curved endoscope system including a curving portion according to the fourth embodiment. In the explanation below, an operation portion 3 has a rectangular shape. The surface of the operation portion 3 in which a UD operation dial is disposed is the front surface. The opposite surface on which the palm abuts is the rear surface. The surface to which a universal cable 5 is coupled is a first side surface. The surface in which an operation input unit 101 is disposed is a second side surface. Moreover, the side to which a grip portion 23 is coupled is a proximal portion or a lower portion, and the opposite side is an upper portion (or upper surface). The endoscope device according to the present embodiment is applied to a medical endoscope device intended to observe, for example, a lumen or body cavity of a living body, and to an industrial endoscope device to observe the internal state of, for example, a pipe or an engine.

The electrically curved endoscope system according to the present embodiment mainly comprises an endoscope body 4 and an unshown drive controller. The endoscope body 4 comprises an insertion portion 2 to be inserted into a lumen, the operation portion 3 provided on the proximal side of the insertion portion 2, the universal cable 5 in which a connector connectable to the drive controller is provided at the end and which includes, for example, a light guide fiber (or optical fiber cable) and a signal cable that are a light guide path of illumination light, and an unshown curving mechanism capable of curving a curving portion 7 provided inside the operation portion 3 and the universal cable 5. The drive controller has a known configuration. For example, the drive controller has an image processor which subjects an obtained video signal to image processing, a universal light source which generates illumination light, a controller (control unit) which performs overall control including the drive control of each component provided in a later-described imaging section and the operation portion, a motor drive power supply which supplies driving electricity to a driving source (power unit: a curving driving motor 31) to drive the curving mechanism, a monitor which displays a processed observation image, and an input device such as a keyboard for setting and selection.

Here, the driving source (motor 31) may be provided inside the operation portion 3 as shown in FIG. 1, or may be provided in a connector of the universal cable 5. When the driving source (motor 31) is provided in the connector of the universal cable 5, the curving mechanism is configured to transmit driving force generated in the driving source (motor 31) to the operation portion 3 via a flexible coil shaft which is provided in the universal cable 5 and which can transmit rotation from one end to the other end. In the case of the following explanation, the driving source (motor 31) is provided in the operation portion 3. As described above, the location of the driving source (motor 31) is not limited to this.

The controller outputs an instruction signal to curve the curving portion 7 to the motor drive power supply in response to the rotational operation (moving portion) of an operation dial 105 (input operation portion 4) of the operation input unit 101 described later, thereby driving the motor 31 to perform a curving operation.

The insertion portion 2 comprises the grip portion 23 on the proximal side to be grasped by the operator, a long flexible tube (flexible tubular portion) 8, the curving portion 7 provided on the distal side of the flexible tube 8, and a distal portion 6 provided on the distal side of the curving portion 7. A forceps opening 25 through which a treatment tool such as a forceps is inserted is provided in the grip portion 23, and a through-hole is formed in the flexible tube 8. Although not shown, the imaging section, an illumination light emission window, and a washing nozzle for washing the imaging section are disposed in the distal surface of the distal portion 6. The distal portion 6 further has a forceps opening connected to the forceps opening introduction 25 through the through-hole.

The curving driving motor 31 serving as the driving source of the curving portion 7 is disposed on the top of the operation portion 3 integrally with the housing of the operation portion.

A UD operation dial 14 which is manually rotated for a curving operation in the vertical (up/down) direction is provided in the front surface of the operation portion 3. In the vicinity of the UD operation dial 14, a UD brake dial 28 to temporarily lock the UD operation dial 14 is disposed. The operation input unit 101 is provided on the second side surface of the operation portion 3. Here, the operation input unit 101 corresponds to an RL operation dial for a curving operation in the right/left (RL) direction. Although not shown, multiple wires are laid in the curving portion 7. One end of each wire is coupled to a motor drive mechanism (curving unit) driven by the motor 31, and the other end is coupled to each of curving pieces that constitute the curving portion 7. The wires pulled by the motor drive mechanism pull the curving pieces, and the curving portion 7 is curved.

In the present embodiment, when grasping the operation portion 3, the operator, by way of example, grasps by abutting, on the universal cable 5, the base part between the thumb and the forefinger, puts the thumb on the UD operation dial 14, puts the palm on the rear side, and puts the little finger or the ring finger on the operation dial 105 of the input operation unit (RL operation unit) 101. Although the input unit having a neutral return mechanism is used for the RL operation of the curving portion in the example suggested in the present embodiment, it should be appreciated that the present invention is not limited to this example. The input unit can also be used as an input unit for a UD operation if the location of the operation dial is simply changed.

Figure 26:
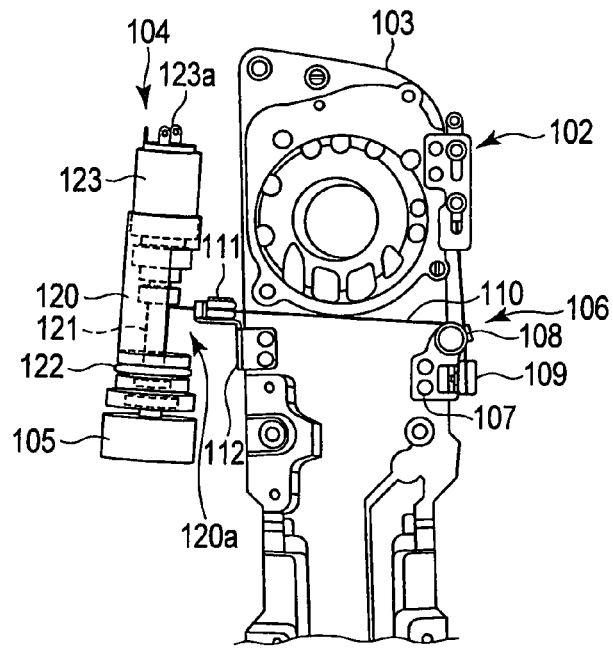
FIG. 26 is a diagram conceptually showing an arrangement relation between the input operation portion and the neutral return mechanism in the input unit located in a substrate seen from the front surface of the substrate in the operation portion.
Figure 27:
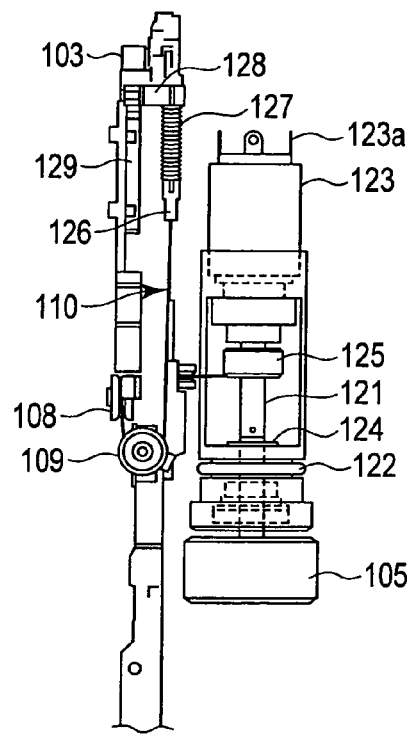
FIG. 27 is a diagram conceptually showing an arrangement relation between the input operation portion and the neutral return mechanism located in the substrate seen from the side surface of the substrate in the operation portion.

FIG. 25 is an arrangement/configuration example of the input operation portion and the neutral return mechanism in the input unit located apart in the operation portion. FIG. 26 conceptually shows an arrangement relation between the input operation portion and the neutral return mechanism located in a substrate seen from the front surface (main surface) of the substrate. FIG. 27 is a diagram conceptually showing an arrangement relation between the input operation portion and the neutral return mechanism seen from the side surface of the substrate.

A substrate 103 on which various electric components are mounted is housed in the operation portion 3. The input unit 101 is separated into an input operation portion (operator) 104 which is an input portion and a neutral return mechanism (force generating unit: return force generating portion) 102. These separated parts are respectively disposed on both sides of the substrate 103, and are drivably coupled by a coupling mechanism (coupler) 106. Although the neutral return mechanism 102 is disposed in the operation portion housing on the side to which the universal cable 5 is coupled in the example shown in the present embodiment, the neutral return mechanism 102 can be basically disposed in a free space in the housing and coupled by the coupling mechanism 106.

Here, the configuration of the input operation portion 4 is described with reference to FIGS. 28A, 28B, and 28C. FIG. 28A is a diagram showing a detailed configuration of the input operation portion. FIG. 28B is a diagram showing the appearance of a bracket of an exterior. FIG. 28C is a diagram showing the configuration of an operator body.

The input operation portion 104 comprises an operator body 114 and a bracket 120.

As shown in FIG. 28C, in the operator body 114, the distal end of an output shaft 121 extending from a potentiometer 123 and the distal end of an operation shaft 133 extending from the operation dial 105 are coupled to each other by fitting a depression and a protrusion provided in these distal ends. A nut 131 and a wire fixing ring 125 are fitted to the output shaft 121. The nut 131 watertightly attaches and fixes, to the bracket 120, the potentiometer 123 (which is not limited to this if it is a component such as an encoder capable of angle detection) which functions as a rotation angle detector to detect the rotation angle of the output shaft 121 (operation dial 105). The wire fixing ring 125 is coupled to a wire 110 which is a long member. A detachment prevention washer 132 such as an E-ring, an O-ring 122, and an adjustment screw 134 are fitted to the operation shaft 133. The detachment prevention washer 132 prevents the side of the operation dial 105 from coming off the bracket 120. The O-ring 122 has a watertight function and functions as a later-described brake. The adjustment screw 134 adjusts the crushed state (braking power) of the O-ring 122. Here, the O-ring 122 and the adjustment screw 134 function as a rotation resistance force generating portion to generate rotation resistance force which cancels the rotation of the output shaft 121.

The bracket 120 has a tubular shape with openings at both ends. The central portion of the bracket 120 is semi-circumferentially cut so that a window 120a is made. This window 120a is formed to be spatially connected to the inside of the operation portion housing when the bracket 120 is attached to the operation portion 3, and is watertightly attached to the operation portion housing.

The operator body 114 partly exposes the operation dial 105 and the potentiometer 123 from the openings at both ends of the bracket 120, and watertightly houses the other parts. The side of the operation dial 105 is fixed so that the operation shaft 133 is coupled to the output shaft 121 by inserting the operation shaft 133 from one opening of the bracket 120 and inserting the detachment prevention washer 132 into a groove formed at a predetermined position in the operation shaft 133. In this case, the entrance of, for example, water into the bracket 120 from the outside is prevented by the crushing of the O-ring 122. The side of the potentiometer 123 is fixed to the bracket 120 with the nut 131 by the insertion of the output shaft 121 from the other opening. In this case, the entrance of, for example, water into the bracket 120 from the outside is prevented by the nut 131. The wire fixing ring 125 is disposed to be seen from the window 120a.

According to this configuration, if the operation dial 105 is rotated, the output shaft 121 of the potentiometer 123 is rotated together, so that a volume value between multiple (e.g. three) output terminals 123a is changed, and an input value can be varied and then output. The terminals 123a are connected to a control section provided in the operation portion, for example, on the substrate 103 through an unshown wiring line, and give instructions as to the rotation direction of a curving driving motor 210 (the curving direction of a curving portion 207).

Now, the neutral return mechanism 102 is described.

Figure 29A:
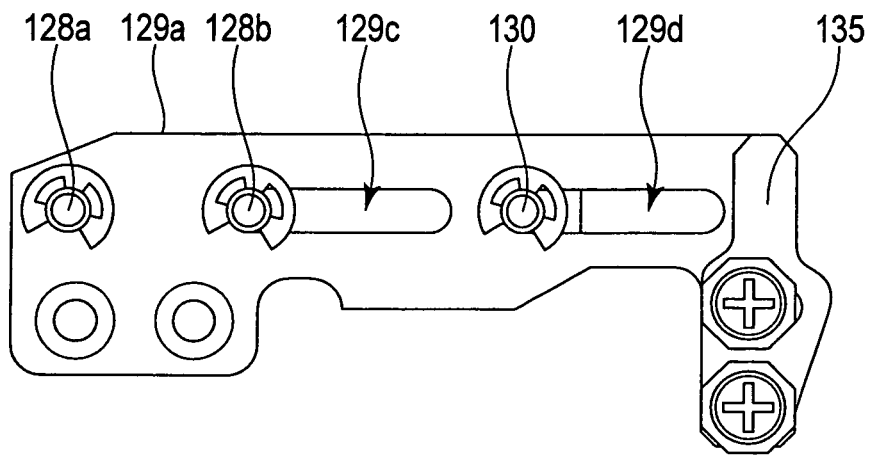
FIG. 29A is a diagram showing the external configuration of the neutral return mechanism seen from above.
Figure 29B:
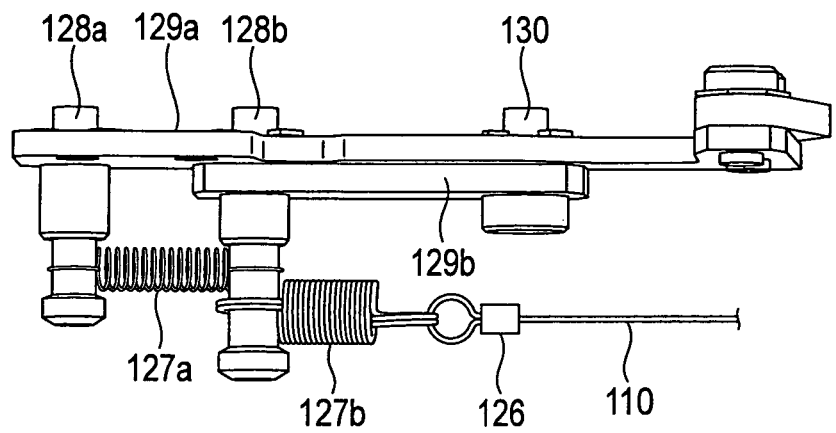
FIG. 29B is a diagram showing the external configuration of the neutral return mechanism seen from the side.

FIG. 29A is a diagram showing the external configuration of the neutral return mechanism 102 seen from above. FIG. 29B is a diagram showing the external configuration of the neutral return mechanism 102 seen from the side. FIG. 30A is a diagram showing the state of the neutral return mechanism 102 in which an operation dial 5 inhibits the slack of the wire 110 in the vicinity of the neutral position. FIG. 30B is a diagram showing how the neutral return mechanism 102 located within an engage range (angle) around the neutral position does not return due to braking force applied to the operation dial 105. FIG. 30C is a diagram showing how the operation dial 105 is rotated so that the neutral return mechanism 102 returns due to elastic force (urging force) surpassing the braking force.

As shown in FIG. 29B, the neutral return mechanism 102 comprises a spring plate 129a for fixing to the substrate 103, a slide plate 129b, a hook 128a fixed to the spring plate 129a, a hook 128b fixed to the slide plate 129b, a coil spring (force generating portion) 127a hooked between the hook 128a and the hook 128b, a coil spring 127b having one end attached to the hook 128b, a wire stop 126 which connects the later-described wire 110 to the other end of the coil spring (force generating portion) 127b, and a positioning plate 135 which positions the spring plate 129a by screwing to the substrate 103.

The material of the wire 110 is not particularly limited as long as the wire 110 endures the pulling by the coil spring 127a and the coil spring 127b and has a low percentage of elongation. For example, the wire 110 is preferably a fluorocarbon line or a PE line used as a fishing line. It is also possible to use an extremely thin rigid metal line used as a guitar string.

Two long holes 129c and 129d arranged in the pulling direction of the wire 110 are formed in the spring plate 129a. The hook 128b is movably fitted in the long hole 129c, and fastened by metal fittings such as an E-ring. Similarly, a slide jig 130 fixed to the slide plate 129b is movably fitted in the long hole 129d, and fastened by a fixing washer such as an E-ring. This configuration enables the slide plate 129b to slide over the spring plate 129a in the pulling direction of the wire 110. The coil spring 127a has elastic force (spring force) lower than the maximum braking force of the O-ring 122, and functions to eliminate the slack of the wire 110.

The engage range according to the present embodiment is the angle range or rotational movement distance of the rotation of the operation dial 105 which is set depending on the curving angle θ1 of the curving portion 207 shown in FIG. 24. Here, the engage range suggests a predetermined range of the rotation angle or the rotational movement distance of the operation dial 105 including, as 0, the neutral position (the position where the curving portion linearly extends) corresponding to the neutral position (the position where the curving portion linearly extends) of the curving portion 207. When the curving portion 207 is at a maximum curving angle θ2, the rotation range of the operation dial 105 corresponding to the range from a curving angle of 0° to the curving angle θ1 is the engage range, and the rotation range of the operation dial corresponding to the range from the curving angle θ1 to the curving angle θ2 is the neutral return range or the return range. This suggests that when the rotational position of the operation dial 105 is located in the neutral return range or the return range, the neutral return mechanism 102 functions as the return force generating portion which generates return force to return the rotational position of the operation dial 105 to the neutral position or to the rotation range (engage range) including the neutral position. The curving angle (curving amount) θ1 is, for example, 70° or less.

If the stop position of the operation dial 105 is in the engage range, the neutral return mechanism 102 activates the braking force of the O-ring 122 to prevent the return of the operation dial 105, and maintains the curving state of the curving portion 7. The actual engage range of the operation dial 105 is determined by the movement distance of the slide plate 129b from the hook 128a, that is, the width (longitudinal length) of the long hole 129c and the position of the hole end.

In the neutral return mechanism 102, the slide plate 129b is moved in response to pulling of the wire 110, and then elastic force operates in a direction in which the coil spring 127b is spread and contracted from the point where the hook 128b and the slide jig 130 abut on the distal side (the side of the positioning plate 135) of the long holes 129c and 129d. Thus, the operation dial 105 is returned to the neutral position or to at least the engage range.

Now, the coupling mechanism 106 is described.

The coupling mechanism 106 is a member which couples the input operation portion 104 to the neutral return mechanism 102. More specifically, the coupling mechanism 106 comprises the wire 110 which couples the wire fixing ring 125 to the wire stop 126, and direction changing portions 107 and 112 which change the pulling direction of the wire 110. Since the input operation portion 104 and the neutral return mechanism 102 are disposed on both sides of the substrate 103, the coupling mechanism 106 according to the present embodiment is a unit which changes the direction to adapt to their pulling directions.

The direction changing portion 107 has a configuration in which two pulleys 108 and 109 that rotate in directions crossing each other at right angles are located close to each other in L-shaped metal fittings. In this example, the pulley 108 is located to rotate parallel to the main surface of the substrate 103, while the pulley 109 is located to rotate parallel to the side surface (end face) of the substrate 103. The direction changing portion 112 has a configuration in which a pulley 111 that rotates in a direction crossing the main surface of the substrate 103 is provided in metal fittings having a projecting support portion.

In the direction changing portion 107, the wire 110 extending parallel to the side surface of the substrate 103 from the wire stop 126 of the neutral return mechanism 102 is received by the pulley 109 and then passed to the pulley 108, so that the wire 110 is changed to a perpendicular direction, that is, the direction of the main surface of the substrate 103. The wire 110 whose direction has been changed traverses the space above the main surface of the substrate 103, and is then connected to the wire fixing ring 125 via the pulley 111 of the direction changing portion 112.

In such a configuration, when the operation dial 105 is rotated, the wire 110 is wound around and pulled by the output shaft 121 and the operation shaft 133. When the wire 110 of the neutral return mechanism 102 is pulled, the slide plate 129b is moved, so that the coil spring 127b is spread beyond the engage range, and the operation dial 105 is returned to the engage range.

As described above, according to the present embodiment, the operation input unit 101 is separated into the input operation portion 104 and the neutral return mechanism 102 which are located apart in the operation portion housing. This allows a degree of freedom in the installation in the housing, and also allows the use of a free space that has heretofore been wasteful. The input operation portion 104 is connected to the neutral return mechanism 102 by a simple configuration, and an increase in weight is thereby inhibited.

The operation input unit 101 is disposed in the operation portion 3 so that the input operation portion 104 and the neutral return mechanism 102 are separately located. Consequently, the change of the weight balance in the operation portion 3 is inhibited, a greater increase of weight on the fingertip side is prevented, and well-balanced grasping is possible as heretofore. Moreover, the adjustment screw 134 is adjusted in the input operation portion 104. Thus, the crushed state of the O-ring 122 can be changed to adjust the braking force, and the braking force can be easily fine-tuned even if the O-ring 122 has a manufacturing variation.

The springs different in elastic force are used in the neutral return mechanism 102. Thus, in a preset engage range, the operation dial 105 is not returned to the engage range even if the finger is released from the operation dial 105, and the curving state of the curving portion 7 can be maintained. When the operation dial 105 is rotationally operated beyond the engage range, the operation dial 105 can be returned to the neutral position or to at least the engage range. This engage range is mechanically set by the movement distance of the slide plate 129b, and can be further fine-tuned by the adjustment of the elastic force of the coil spring 127a and the braking force resulting from the O-ring 122. At the start of the neutral return, the return of the operation dial 105 can be slowly started by the adjustment of the braking force resulting from the O-ring 122.

In the present embodiment, the input operation portion 104 is coupled to the neutral return mechanism 102 by the wire 110 which is a long member. However, the long member may be formed by an elastic member such as rubber or a spring which spreads and generates elastic force instead of the wire 110.

Fifth Embodiment

Now, the fifth embodiment is described.

Figure 32A:
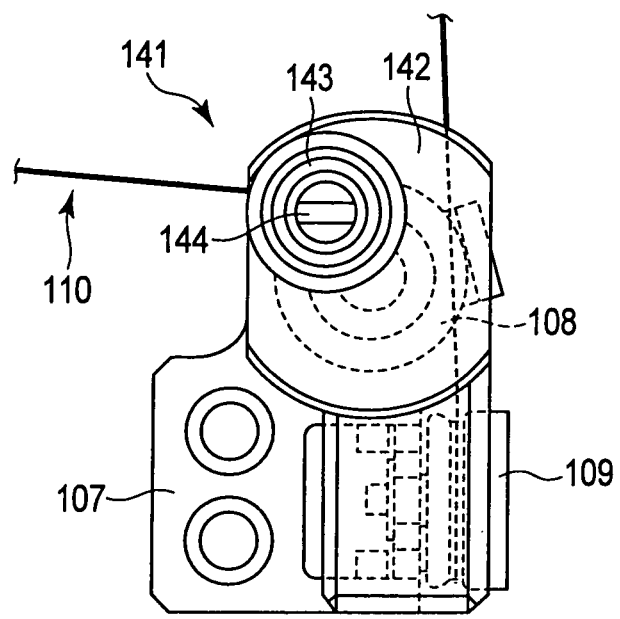
FIG. 32A is a diagram showing the braking mechanism seen from the front.
Figure 32B:
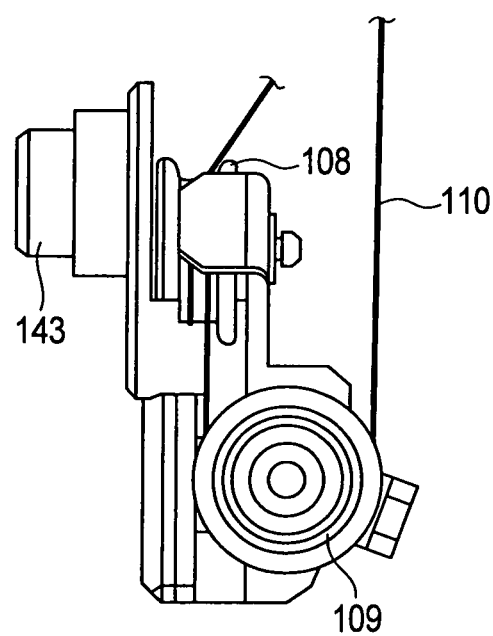
FIG. 32B is a diagram showing the braking mechanism seen from the side.

FIG. 31 is a diagram showing a conceptual configuration of an input unit equipped with a braking mechanism according to the fifth embodiment. FIG. 32A is a diagram showing the braking mechanism seen from the front. FIG. 32B is a diagram showing the braking mechanism seen from the side. FIG. 32C is a diagram showing the braking mechanism seen obliquely from above. FIG. 32D is a diagram showing the braking mechanism seen obliquely from below. FIG. 32E is a diagram showing the braking mechanism seen obliquely from the rear. The present embodiment is different from the first embodiment described above in the configuration of the braking mechanism in the input unit, and is equal in configuration in other respects.

As shown in FIG. 31, in the configuration according to the present embodiment, a braking mechanism 141 is provided in a direction changing portion 107 of a coupling mechanism 106 instead of the braking function by the O-ring 122 in the fourth embodiment described above. In the fifth embodiment, the O-ring 122 is not used as a brake but is used as a watertight waterproof member.

As shown in FIGS. 32A, 32B, and 32C, the braking mechanism 141 comprises a braking cover 142 fitted to the metal fittings of the direction changing portion 107, a braking jig 143 provided in the braking cover 142, a braking screw 144 for braking force adjustment, and a sliding member 145 serving as a braking portion. The braking mechanism 141 is configured to apply the brakes by pushing the sliding member 145 against a pulley 108 of the direction changing portion 107.

As shown in FIGS. 32C and 32D, the braking cover 142 integrally comprises an engagement plate portion 142a provided with hooks 142c to be fitted in an opening in the metal fittings for locking, and a braking plate portion 142b which faces the pulley 108 when fitted to the metal fittings.

A cylindrical erected fixing portion is formed in the braking plate portion 142b, and the cylindrical braking jig 143 is fitted in the fixing portion. An internal thread is formed in the center of the braking jig 143, and the braking screw 144 is screwed to the internal thread. A pad-like sliding member 145 which functions as a brake is provided on the distal side of the braking screw 144. If the braking screw 144 is screwed in, the sliding member 145 is pressed out of the rear side (the surface facing the pulley 108) of the braking plate portion 142b, pressed against a flange surface of the pulley 108, and brakes the pulley 108 in accordance with the pressure. A wire 110 has one end fixed to an output shaft 121 by a wire fixing ring 125, and is wound around the pulley 108 on the way. The pulley 108 is rotated in accordance with the pulling operation of the wire 110. Rotational resistance which prevents rotation is applied to the pulley 108 by the sliding member 145, and the movement of the wire 110 is thereby inhibited. That is, the braking mechanism 141 can generate the rotational resistance which prevents the rotation of the output shaft 121. Thus, the braking mechanism 141 functions as a rotation resistance force generating portion which generates rotation resistance force to inhibit return force that returns an operation dial 105 to the neutral position in the rotation range including the neutral position. An elastic member or a resin material such as a rubber material can be used for the sliding member 145.

In this braking mechanism 141, the wire 110 may slide because of slippage between the pulley 108 and the wire 110 even if the pulley 108 is stopped. In this case, as shown in FIG. 32B, the wire 110 needs to make at least one round of the pulley 108 to stop the slippage of the wire 110.

According to the present embodiment described above, advantageous effects equivalent to those in the above fourth embodiment can be obtained. In the first embodiment, the watertight function and the braking function are required for the O-ring 122. Meanwhile, in the present embodiment, the watertight function alone is required for the O-ring 122, and the braking mechanism 141 is separately disposed. Therefore, deterioration of the durability of the O-ring 122 is inhibited, and the braking function of wide application can be provided by the selection of the material of the sliding member 145.

Sixth Embodiment

Now, the sixth embodiment is described.

Figure 33B:
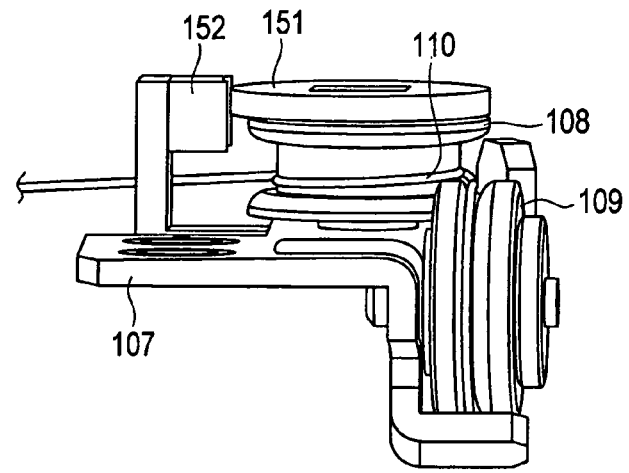
FIG. 33B is a diagram showing the braking mechanism shown in FIG. 33A seen from the side.

FIG. 33A is a diagram showing a braking mechanism according to the sixth embodiment seen from the front. FIG. 33B is a diagram showing the braking mechanism seen from the side. In the configuration according to the fifth embodiment described above, the sliding member abuts on the pulley to achieve braking. However, a braking mechanism 150 according to the present embodiment is configured to press a sliding member 152 against the side surface of a cam 151 integrated with a pulley 108 to achieve braking.

The present embodiment is different from the fourth embodiment described above in the configuration of the braking mechanism in the input unit, and is equal in configuration in other respects.

The braking mechanism 150 according to the sixth embodiment comprises the disk-shaped brake cam plate 151 fixed to a flange surface of the pulley 108, and the sliding member 152 which is pressed against the side surface of the brake cam plate 151 to achieve braking. The brake cam plate 151 has a disk shape with semicircularly different radiuses R1 and R2 (R1<R2). An outer circumferential surface having the radius R1 is a braking side surface 151a, and an outer circumferential surface having the radius R2 is a non-braking side surface 151b.

The sliding member 152 is located in the vicinity of this brake cam plate 151. The sliding member 152 is moved back and forth by an unshown movement mechanism so that the sliding member 152 can be pressed against the braking side surface 151a. Basically, the sliding member 152 is located in the central position of the braking side surface 151a. In the present embodiment, the braking side surface 151a of the sliding member 152 which abuts on the plate surface is shaped to curve along the circumferential shape of the brake cam plate 151 so that braking force is effectively generated.

Although the brake cam plate 151 is divided into a semi-braking range and a non-braking range, the ratio can be changed in accordance with design specifications. The size of the radius can be properly set. The braking force can also be set and changed by the change of the thickness of not only the curved side surface but also the brake cam plate 151, that is, the area to abut on the sliding member 152.

The wire 110 has one end fixed to an output shaft 121 by a wire fixing ring 125, and is wound around the pulley 108 on the way. The pulley 108 is rotated in accordance with the pulling operation of the wire 110. Rotational resistance which prevents rotation is applied to the pulley 108 when the sliding member 152 is pressed against the integral brake cam plate 151, and the movement of the wire 110 is inhibited. That is, it is possible to generate the rotational resistance which prevents the rotation of the output shaft 121. Thus, the braking mechanism 150 functions as a rotation resistance force generating portion which generates rotation resistance force to inhibit return force that returns an operation dial 105 to the neutral position in the rotation range including the neutral position.

Although the brake cam plate 151 having a uniform thickness is suggested according to the present embodiment, braking force that is transmitted during the rotation of the operation dial 105 can be varied in stages by a partial change of the thickness (the height of the braking side surface 151a). For example, the central side and both ends of the braking side surface 151a are formed with thickness (or shapes) varying in stages. Thus, when the braking force suddenly changes, for example, becomes heavier, the operator can perceive by the fingertip that the operation dial goes beyond the engage range if further rotationally operated. If the operator experientially knows the curving angle of a curving portion 7 at the end of the engage range, the operator can easily estimate the curving state at the moment in accordance with the change of the braking force perceived in the fingertip. Therefore, when the braking side surface 151a has stages of thickness within a range in which the change of the braking force can be perceived by the fingertip, the curving angle at the moment can be estimated.

In the configuration according to the present embodiment, when the curving portion 7 reaches the maximum curving angle in one direction from a linear state, the rotation angle of the brake cam plate 151 resulting from the rotational operation of the operation dial 105 is set within an angle in which the braking side surface 151a is detached from the sliding member 152 from the central position (the position where the central position of the sliding member 152 faces the central position of the brake cam plate 151) to reach the opposite end of the non-braking side surface 151b. This can be achieved by the setting of the diameter of the pulley 108 and the diameter of the brake cam plate 151.

In the braking mechanism 150 as well, the wire 110 may slide because of slippage between the pulley 108 and the wire 110 even if the pulley 108 is stopped. In this case, as shown in FIG. 33B, the wire 110 needs to make at least one round of the pulley 108 to stop the slippage of the wire 110.

As described above, according to the input unit in the present embodiment, braking force can be generated by the simple configuration of the braking mechanism, in addition to the advantageous effects according to the fourth embodiment described above.

Seventh Embodiment

Now, the seventh embodiment is described.

Figure 34A:
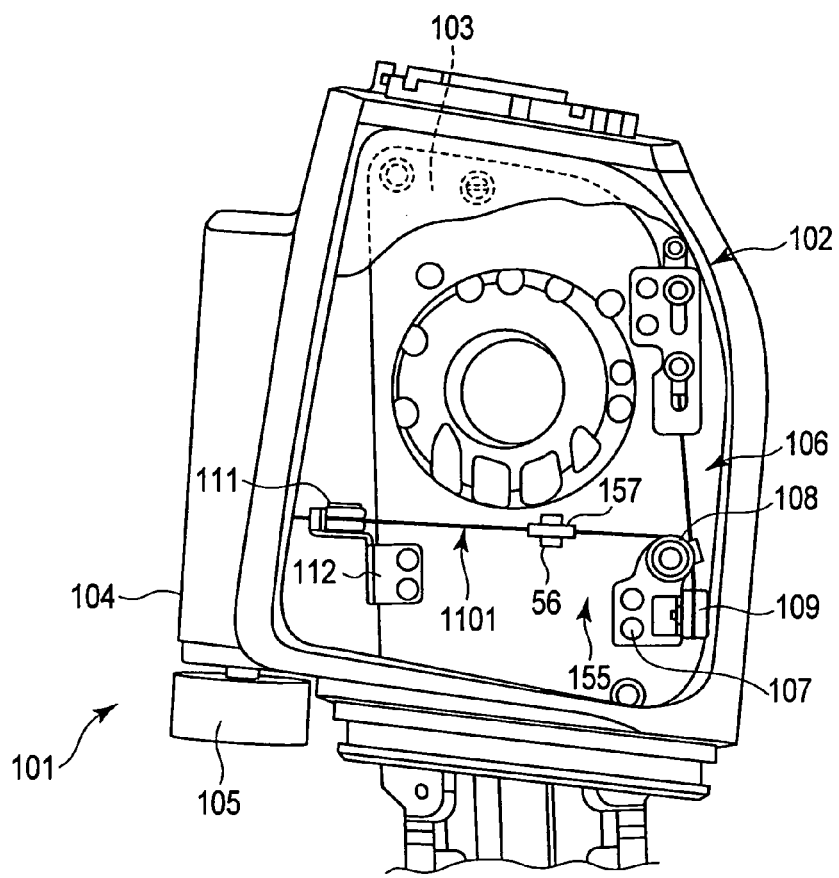
FIG. 34A is a diagram showing a braking mechanism provided in an operation portion according to a seventh embodiment seen from the front.
Figure 34B:
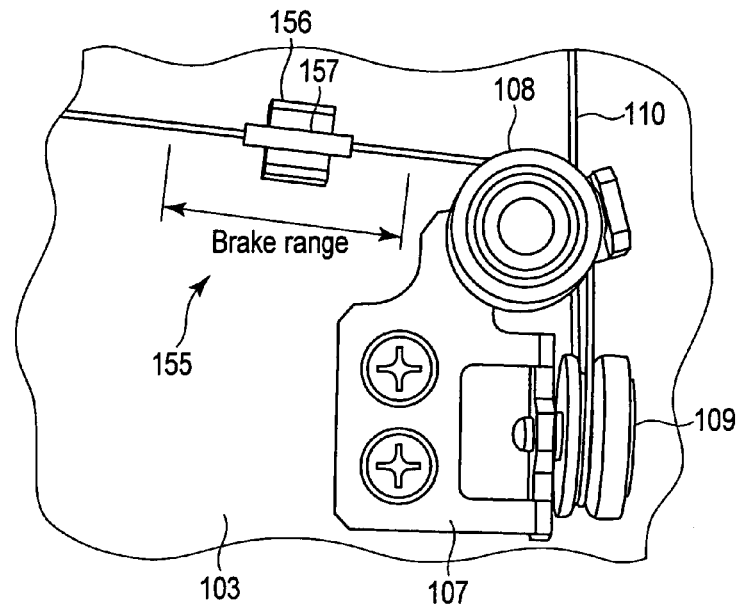
FIG. 34B is a diagram showing a detailed configuration of the braking mechanism shown in FIG. 34A.

FIG. 34A is a diagram showing a braking mechanism provided in an operation portion according to the fourth embodiment seen from the front. FIG. 34B is a diagram showing a detailed configuration of the braking mechanism. The present embodiment is different from the fourth embodiment described above in the configuration of the braking mechanism in the input unit, and is equal in configuration in other respects.

As shown in FIG. 34A, a braking mechanism 155 according to the present embodiment comprises a sliding member 156 disposed on a substrate 103, and an annular braking member 157 fitted in a wire 110 which slides over the sliding member 156.

A U-groove is formed in the center of the sliding member 156, and the braking member 157 is formed to slide over the wall surface of the U-groove. A braking range, that is, engage range in the braking mechanism 155 is a range in which the braking member 157 is in contact with the U-groove of the sliding member 156. The curving portion 7 is linear at the position (neutral position) where the central position of the U-groove overlaps the central position of the braking member 157.

In this configuration, when an operation dial 105 is rotationally operated, the braking member 157 is moved in response to the movement of the wire 110 and may go beyond the braking range by the sliding member 156, that is, the engage range. In this case, elastic force resulting from the above-mentioned neutral return mechanism 102 causes an operation dial 5 to return to the neutral position or the engage range.

The wire 110 has one end fixed to an output shaft 121 by a wire fixing ring 125, and is wound around the pulley 108 on the way. The pulley 108 is rotated in accordance with the pulling operation of the wire 110.

In the braking mechanism 155, the braking member 157 holds the wire 110 and generates frictional resistance to prevent a pulling operation, and thus generates rotational resistance force to prevent the rotation of the output shaft 121. That is, the braking mechanism 155 functions as a rotation resistance force generating portion which generates rotation resistance force to inhibit return force that returns the operation dial 105 to the neutral position in the rotation range including the neutral position.

According to the input unit in the present embodiment, the braking mechanism can be obtained by an extremely simple configuration and can be small-sized, so that an increase in the weight can be reduced. The engage range can be changed merely by the change of the length of the sliding member 156 (the length of the groove). Although the braking mechanism 155 shown in the present embodiment is configured by the combination of a pair of sliding members 156 and the braking member 157, the present invention is not limited to this. More than one sliding member 156 and the braking member 157 can be located apart on a substrate 3.

Eighth Embodiment

Now, the eighth embodiment is described.

Figure 35A:
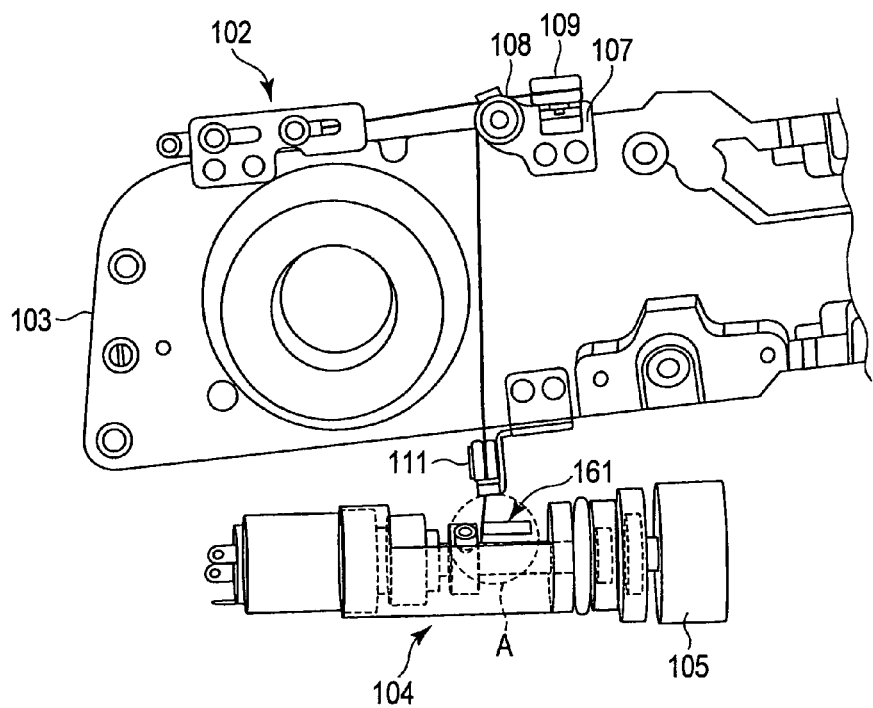
FIG. 35A is a diagram showing a braking mechanism provided in an operation portion according to an eighth embodiment seen from the front.
Figure 35B:
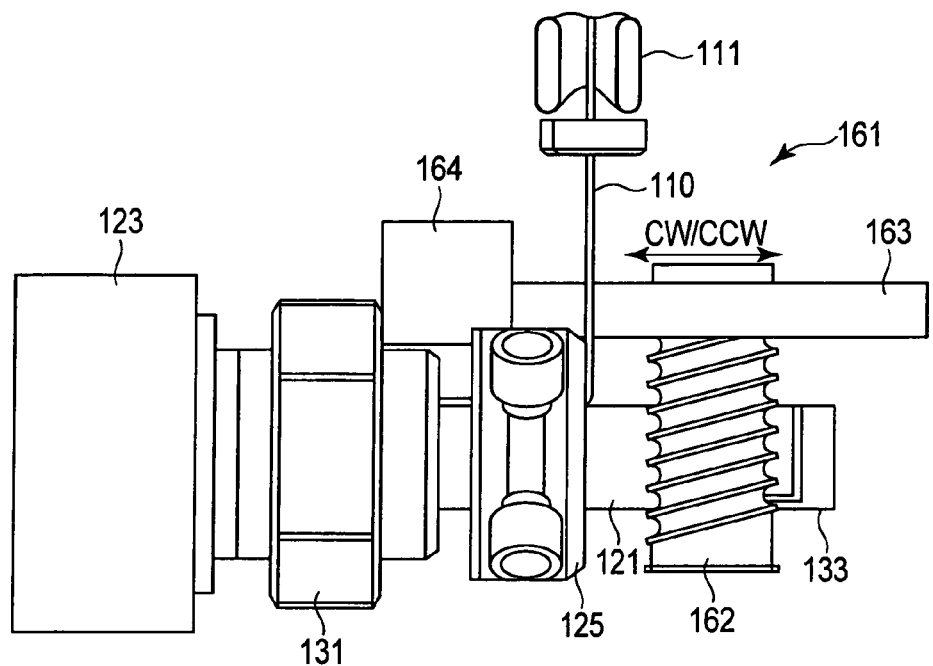
FIG. 35B is a diagram showing a detailed configuration of the braking mechanism shown in FIG. 35A.

FIG. 35A is a diagram showing a braking mechanism provided in an operation portion according to the fifth embodiment seen from the front. FIG. 35B is a diagram showing a detailed configuration of the braking mechanism. The present embodiment is different from the fourth embodiment described above in the configuration of the braking mechanism in a input unit, and is equal in configuration in other respects.

A braking mechanism 161 according to the present embodiment comprises a worm gear (rotation transmitting member) 162 which is toothed with a gear (not shown) formed in an output shaft 121, a plate-shaped slide member 163 in which a gear (not shown) is formed on the rear side which is toothed with the worm gear 162, and a sliding member 164 which slides on a flat braking surface of the slide member 163.

In this braking mechanism 161, the output shaft 121 coupled to an operation shaft 133 is rotated by the rotational operation of the operation dial 105. The rotation of the output shaft 121 is transmitted to the worm gear 162 toothed with the output shaft 121 (CW/CCW). In accordance with the rotation direction of the worm gear 162, the slide member 163 is moved, so that the sliding member 164 slides over the braking surface of the slide member 163, and braking force is generated. The slide member 163 is moved in one of repetition directions in accordance with the rotation direction (CW/CCW) of the operation dial 105.

The neutral position of the operation dial 105 is a position at which the largest area of the slide member 163 abuts on the sliding member 164. In FIG. 35B, the end of the slide member 163 is located closest to a nut 131. In response to the rotational operation of the operation dial 105, the slide member 163 slides over the sliding member 164, and comes off the sliding member 164. In the present embodiment, the range in which the slide member 163 is in abutment with the sliding member 164 is the engage range where braking force is effective. That means that rotation resistance force which can prevent the rotation of the output shaft 121 can be generated by the generation of frictional resistance in the abutment surface between the slide member 163 and the sliding member 164. That is, the braking mechanism 161 functions as a rotation resistance force generating portion which generates rotation resistance force to inhibit return force that returns the operation dial 105 to the neutral position in the rotation range including the neutral position.

As described above, according to the present embodiment, the braking mechanism is located not on the substrate 103 but in the vicinity of an operator body 114 in a bracket 120 of the input unit. Therefore, the present embodiment can be easily implemented even if there is no space in a unit housing.

Ninth Embodiment

Now, the ninth embodiment is described.

Figure 36A:
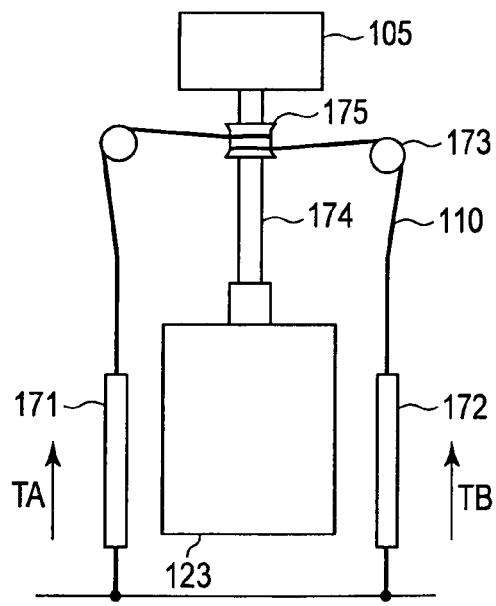
FIG. 36A is a diagram showing a conceptual configuration of a braking mechanism provided in an operation portion according to a ninth embodiment.

FIG. 36A is a diagram showing a conceptual configuration of a neutral return mechanism provided in an operation portion according to the ninth embodiment. FIG. 36B is a diagram showing the state of an elastic member when an operation dial is rotated in an m-direction. FIG. 36C is a diagram showing the state of the elastic member when the operation dial is rotated in an n-direction. The present embodiment is different from the fourth embodiment described above in the configuration of neutral return mechanisms in an input unit, and is equal in configuration in other respects.

In the present embodiment, an operation dial 105 is attached to the distal end of a shaft (an output shaft 121 or an operation shaft 133) 174 of a potentiometer 123. A pulley 175 is fitted to the middle part of the shaft 174 (or the operation shaft 133). Neutral return mechanisms 171 and 172 having the same elastic force (tensile force) each have one end fixed to the housing of an operation portion 3 or a bracket 120 so that the potentiometer 123 intervenes in between. The neutral return mechanisms 171 and 172 according to the present embodiment have a configuration equivalent to that in the fourth embodiment described above. Both ends of a wire 110 are fixedly connected to the neutral return mechanisms 171 and 172 via two pulleys 173 and 175 on the way. That is, in FIG. 36A, the wire 110 makes a round of the pulley 175 at the central position of its length, is fixedly connected to the neutral return mechanisms 171 and 172 through the pulleys 173, and is stopped with equal tensile forces TA and TB that are balanced. The position of the operation dial 105 in this case is set to the neutral position.

If the operation dial 105 is rotationally operated in the m-direction from this state as shown in FIG. 36B, the pulley 175 is integrally rotated, and sends the wire 110 toward the neutral return mechanism 172. Elastic force operates from the point where tensile force TAr (TAr>TBr) of the neutral return mechanism 171 goes beyond the engage range, and the operation dial 105 is returned to the original neutral position or the engage range. On the other hand, if the operation dial 105 is rotationally operated in the n-direction as shown in FIG. 36C, the pulley 175 is rotated, and sends the wire 110 toward the neutral return mechanism 171. Elastic force operates from the point where tensile force TBl (TAi>TBi) of the neutral return mechanism 172 goes beyond the engage range, and the operation dial 105 is returned to the original neutral position or the engage range.

The neutral return mechanisms 171 and 172 are located in the vicinity of the potentiometer 123 in the conceptual configuration shown in FIG. 36A according to the present embodiment, but can be separately located in practice. Although the central position (length) of the wire 110 is set to be wound around the pulley 175 provided on the shaft in the present embodiment, the right and left parts of the wire 110 do not have to be equal in length. That is, the tensile force when the operation dial 105 is at the neutral position or in the engage range has only to be applied to the pulley 175 by the neutral return mechanisms 171 and 172. Thus, by the adjustment of spring force, the same tensile force can be applied to the pulley 175 not at the central position where the wire 110 is equal in length on both sides but at the position where the wire 110 is different in length on both sides.

As described above, the input unit according to the present embodiment is pulled from the right and left by the same tensile force due to the wire 110, so that the structure which supports the shaft can be simpler than the structure that winds the wire around the shaft.

Tenth Embodiment

FIG. 37 is a diagram showing a conceptual configuration of a neutral return mechanism provided in an operation portion according to the tenth embodiment. In a double-bearing potentiometer 123 provided with an output shaft that is passed therethrough, an operator body 181 according to the present embodiment has an operation dial 105 attached to one end of the output shaft, and a wire fixer 184 of a wire 110 attached to the other end. One end of the wire 110 is fixed to the wire fixer 184. The other end of the wire 110 is changed toward the extending direction of the output shaft by a pulley 183, and then faces toward the operation dial 105 and is coupled to a neutral return mechanism 182. The neutral return mechanism 182 has a configuration similar to that of the neutral return mechanism 102 according to the fourth embodiment, and is fixed to the above-mentioned substrate 103, an operation portion housing, or a bracket 120 of an input operation portion 104.

In this configuration, if the operation dial 105 is rotationally operated in one of the directions, the wire 110 is wound around the output shaft so that a spring in the neutral return mechanism 182 is pulled. As a result, elastic force is generated so that the operation dial 105 is returned to the neutral position or the engage range.

The present embodiment enables a simpler structure and a smaller size, in addition to the advantageous effects according to the fourth embodiment.

Eleventh Embodiment

FIG. 38 is a diagram showing a conceptual configuration of a neutral return mechanism provided in an operation portion according to the eleventh embodiment. In an operator body 185 according to the present embodiment, an operation dial 105 is attached to the end of an output shaft of a potentiometer 123, and a wire fixer is attached to the output shaft to fix one end of a wire 110. The other end of the wire 110 is changed toward the extending direction of the output shaft by a drum roller 187, and then faces toward the potentiometer 123 and is coupled to a neutral return mechanism 186. The neutral return mechanism 186 has a configuration similar to that of the neutral return mechanism 102 according to the fourth embodiment, and is fixed to the above-mentioned substrate 103, an operation portion housing, or a bracket 120 of an input operation portion 104.

In this configuration, if the operation dial 105 is rotationally operated in one of the directions, the wire 110 is wound around the output shaft so that a spring in the neutral return mechanism 186 is pulled. As a result, elastic force is generated so that the operation dial 105 is returned to the neutral position or the engage range.

The present embodiment enables a simpler structure of an input unit and a smaller size, in addition to the advantageous effects according to the fourth embodiment.

Twelfth Embodiment

FIG. 39 is a diagram showing a conceptual configuration of a neutral return mechanism provided in an operation portion according to the twelfth embodiment. In an operator body 190 according to the present embodiment, an operation dial 105 is attached to the end of an output shaft of a potentiometer 123. A wire 110 fixed to two neutral return mechanisms 191 and 192 that are located on both rear sides of the potentiometer 123 extends and is wound around the output shaft in the figure of eight. The two neutral return mechanisms 191 and 192 have a configuration similar to that of the neutral return mechanism 102 according to the fourth embodiment.

In this configuration, if the operation dial 105 is rotationally operated in one of the directions, the wire 110 is wound around the output shaft. For example, if the wire 110 is paid out toward the neutral return mechanism 191, a spring in the neutral return mechanism 192 is pulled, and elastic force is then generated so that the operation dial 105 is returned to the neutral position or the engage range. If the operation dial 105 is rotationally operated in the other direction, the wire 110 is paid out toward the neutral return mechanism 192, a spring in the neutral return mechanism 191 is pulled, and elastic force is then generated so that the operation dial 105 is returned to the neutral position or the engage range. In this case, the surface of the output shaft is preferably treated, for example, coated with an elastic material so that the wire 110 is easily entwined.

The present embodiment enables a simpler structure and a smaller size, in addition to the advantageous effects according to the fourth embodiment.

Thirteenth Embodiment

FIG. 40 is a diagram showing a conceptual configuration of a neutral return mechanism provided in an operation portion according to the thirteenth embodiment. In an operator body 193 according to the present embodiment, an operation dial 105 is attached to the end of an output shaft of a potentiometer 123. A bevel wheel 194 is fitted to the middle part of the output shaft of the potentiometer 123. A wire fixing roller 195 integrally having a bevel wheel 195a which is toothed with the bevel wheel 194 is provided. One end of a wire 110 is fixed to the wire fixing roller 195, extends in the direction of the output shaft. The other end of the wire 110 is connected to a neutral return mechanism 196. The neutral return mechanism 196 has a configuration similar to that of the neutral return mechanism 102 according to the fourth embodiment.

In this configuration, if the operation dial 105 is rotationally operated in one of the directions, the wire 110 is wound around the wire fixing roller 195, a spring in the neutral return mechanism 196 is pulled, and elastic force is then generated so that the operation dial 105 is returned to the neutral position or the engage range.

The present embodiment enables a simpler structure of an input unit and a smaller size, in addition to the advantageous effects according to the fourth embodiment.

Fourteenth Embodiment

FIG. 41 is a diagram showing a conceptual configuration of an input operation portion 197 of an operation portion according to the fourteenth embodiment.

In the fourth embodiment described above, the distal end of the output shaft of the potentiometer 123 and the distal end of the operation shaft extending from the operation dial 105 are coupled to each other by fitting the depression and the protrusion provided in these distal ends. In this configuration, the output shaft and the operation shaft integrally rotate one to one in the rotational operation of the operation dial.

In the configuration according to the present embodiment, a gear 198 is attached to the distal end of an operation shaft, and a planetary gear 199 is attached to the distal end of an output shaft. In this configuration, the rotation amount (rotation angle) of the output shaft is larger than the rotation amount (rotation angle) of the operation shaft resulting from the rotational operation of the operation dial so that the stroke of a spring in a neutral return mechanism is shorter.

According to the present embodiment, the size and weight of an input unit can be reduced by the size reduction of the neutral return mechanism. In particular, the input operation portion and the neutral return mechanism are located apart in the operation portion in the configuration according to the present embodiment. Therefore, the neutral return mechanism is reduced in size and is thus more easily located even in a small space. In the examples described in the above fourth to eleventh embodiments, the wire 110 having a low percentage of elongation is applied. In contrast, an elastic resin wire such as a nylon (registered trademark) wire can be applied so that the stroke of the spring in the neutral return mechanism is shorter.

Fifteenth Embodiment

Now, the fifteenth embodiment is described.

FIG. 42A is a diagram showing a conceptual configuration of a braking mechanism provided in an operation portion according to the fifteenth embodiment. FIG. 42B is a diagram showing a return range when the operation dial is rotated. FIG. 42C is a diagram showing a section A-A of FIG. 42A. The present embodiment is different from the fourth embodiment described above in the configuration of the braking mechanism in the input unit, and is equal in configuration in other respects.

In the braking mechanism according to the present embodiment, an operation dial 105 which is exposed to the outside is watertightly attached to the distal end of an output shaft 201 of a potentiometer 123 in an operation portion housing. A movable arm 202 which is spirally threaded and which has a rounded arm distal end is movably screwed to the output shaft 201. A rotation stop member 204 is disposed on the movable arm 202, and provided with a sliding member 203 over which the arm distal end of the movable arm 202 slides. Moreover, a rotation detection sensor 205 which detects the rotation of the output shaft of the potentiometer 123 is connected.

As shown in FIG. 42C, a groove through which the arm distal end can pass is formed in the rotation stop member 204. As shown in FIG. 49B, the sliding member 203 which is made of an elastic member and which is provided with a trapezoidal protrusion is mounted in the groove.

In the sliding member 203, the protrusion against which the arm distal end passing through the groove is pressed functions as a braking member, and its braking range corresponds to the engage range. The range from a central position 0 of a braking range L1 to both protrusion ends corresponds to a curving range θ1 shown in FIG. 24, and is the engage range. A range L2 up to a maximum movement position beyond the protrusion end is the neutral return range or the return range. The neutral return range or the return range suggests that the arm distal end, that is, the operation dial 105 is returned to the neutral position or the engage range. If the movable arm 202 is brought into abutment with the sliding member 203 to generate frictional resistance, rotation resistance which prevents the rotation of the output shaft 201 can be generated. That is, the sliding member 203 and the movable arm 202 function as a rotation resistance force generating portion which generates rotation resistance force to inhibit return force that returns the operation dial 105 to the neutral position in the rotation range including the neutral position.

The present embodiment enables a simpler structure of the input unit and a smaller size, in addition to the advantageous effects according to the fourth embodiment.

While the embodiments have been described above, the present invention is not limited to the embodiments described above, and it is apparent to those skilled in the art that various improvements and modifications can be made without departing from the spirit of the invention.

According to the present invention, an insertion device comprising an operation portion is provided. The operation portion maintains the state of a dial portion which rotates and indicates a curving operation of an insertion portion in a predetermined rotation angle range, and returns the indicated position of the dial portion to the rotation angle range including an initial position when the dial portion is rotated out of the rotation angle range.

The embodiments according to the present invention described above include the following contents:

(1) An insertion device comprising:
a curving portion curvable in a first direction;
a rectangular grip portion having a longitudinal axis;
a curving unit which is coupled to the grip and which has therein a first curving mechanism configured to curve the curving portion in the first direction;
an input unit which is coupled to the grip or the curving unit and which has an input portion, an operation input to operate the curving portion movable in a direction substantially perpendicular to the longitudinal axis being input to the input portion;
a power unit which is coupled to the first curving mechanism and which generates driving force to curve and drive the curving portion;
a control unit which outputs, to the power unit, a control signal to curve and control the curving portion in accordance with an input amount of the operation input;
an engagement portion which is engaged movably together with the input portion;
a force generating portion which generates force to pull the input portion in a direction opposite to the movement direction of the input portion when pulled by the input portion; and
a force generating unit which is provided apart from the input unit and which has a fixing portion configured to fix a part of the force generating portion to the grip or the curving unit.

(2) The insertion device according to the section (1), wherein the input unit is provided to face the location of a thumb of a hand grasping the grip across the longitudinal axis.

(3) The insertion device according to the section (2), wherein the curving portion is curvable in a second direction which crosses the first direction at right angles,
the curving unit has a dial, the dial having a first rotation shaft, an operation input to curve the curving portion in the second direction being input to the dial, and
the curving unit has a second curving mechanism which curves the curving portion in the second direction together with the rotation of the dial around the first rotation shaft.

(4) The insertion device according to the section (2), wherein the input portion includes a second rotation shaft extending in the longitudinal axis direction, and a dial which rotates together with the second rotation shaft, and
the control unit detects a rotation amount of the second rotation shaft as the input amount.

(5) The insertion device according to the section (1), wherein the force generating portion includes a flexible long wire, and a spring coupled to the wire, and the force generating portion is stretched between the engagement portion and the fixing portion.

(6) The insertion device according to the section (1), wherein the force generating portion comprises a flexible long elastic wire, and
the force generating portion is stretched between the engagement portion and the fixing portion.

(7) The insertion device according to the section (1), wherein the force generating portion has a flexible long wire, a first spring connected to one end of the wire, and a second spring connected to the other end of the wire,
the fixing portion includes a first fixing portion which fixes the first spring to the grip or the curving unit, and a second fixing portion which fixes the second spring to the grip or the curving unit, and
the force generating unit has a middle portion of the wire wound around the second rotation shaft.

(8) The insertion device according to the section (5) to the section (7), further comprising a path defining portion which defines a path of the wire; and
a resistance applying portion which applies sliding resistance to the path defining portion or the wire.

(9) The insertion device according to the section (8), wherein an amount of curving by the control unit in response to the input amount at a position where the sliding resistance and force to pull the input portion are balanced is equal to or less than a predetermined curving amount.

(10) The insertion device according to the section (9), wherein the predetermined curving amount is less than a maximum curving angle of the curving portion.

(11) The insertion device according to the section (9), wherein the predetermined curving angle is 70° or less.

(12) An endoscope device characterized by comprising:

an insertion portion having, on a distal side, a curving portion which curves in one axial direction; and an operation portion which is provided on a proximal side of the operation portion and which has a curving operation input portion configured to be rotationally operated to input an instruction to curve the curving portion, the curving operation input portion including an elastic member having one end attached to a frame body of the curving operation input portion, an abutting portion located at the other end of the elastic member, and an acting portion which moves in accordance with a rotational operation input to abut on the abutting portion and compress the elastic member, wherein a movement amount of the acting portion is adapted to a curving operation input amount of the curving portion in one axial direction, and after the rotational operation input to the curving operation input portion is stopped while the acting portion is in abutment with the abutting portion to compress the elastic member, the acting portion returns to a range in which elastic force resulting from the elastic member is ineffective.

(13) The endoscope device according to the section (12), characterized in that the elastic force ineffective range is set in such a way that a neutral position of the acting portion of the curving operation input portion where the curving portion is not curved is located apart from the abutting portion when the elastic member has a natural length, and when the acting portion is in the elastic force ineffective range, the curving portion includes a condition in which the curving portion is curved in the one axial direction.

(14) The endoscope device characterized in that a range of the condition in which the curving portion is curved in the one axial direction is set to a range suitable for insertion or a treatment.

(15) The endoscope device characterized in that the elastic force ineffective range is set between a neutral position of the acting portion of the curving operation input portion where the curving portion is linear and a position where the elastic member having a natural length abuts on the abutting portion, and when the acting portion is in the elastic force ineffective range, the curving portion is not curved in the one axial direction.

(16) The endoscope device characterized in that when the acting portion is the elastic force ineffective range, the curving state of the curving portion in the one axial direction is known.

(17) The endoscope device characterized in that the elastic member is housed in a spiral groove formed in the frame body of the curving operation input portion.

(18) The endoscope device characterized in that the one axial direction is a leftward direction or a rightward direction, the elastic member has a leftward curving elastic member and a leftward curving abutting portion which curve the curving portion leftward, and the abutting portion has a rightward curving elastic member and a rightward curving abutting portion which curve the curving portion rightward, and the leftward curving elastic member and the leftward curving abutting portion, and the rightward curving elastic member and the rightward curving abutting portion are vertically separately located with respect to the acting portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
   a curving portion which is provided in an insertion portion and curvable between a linear state and a curving state at a maximum curving angle;
   an operation input unit which is operated by an operator and actuated to curve the curving portion in accordance with the operation;
   a first elastic member which generates returning force in a first direction by elastic force;
   a second elastic member which generates returning force in a second direction opposite to the first direction by elastic force; and
   an acting portion that is provided in the operation input unit, and that abuts the first elastic member or the second elastic member to compress the first elastic member or the second elastic member when the curving portion is curved at a predetermined angle or more in accordance with actuation of the operation input unit, and the acting portion configured to be separated from both the first elastic member and the second elastic member when the curving portion is curved at an angle smaller than the predetermined angle.

2. The insertion device according to claim 1, wherein the returning force generating portion includes a first spring which generates the returning force in a first direction and a second spring which generates the returning force in a second direction opposite to the first direction.

3. The insertion device according to claim 1, wherein the acting portion comprises a lever which is abutable on the elastic member.

* * * * *

UNITED STATES PATENT AND TRADEMARK OFFICE
CERTIFICATE OF CORRECTION

PATENT NO. : 9,237,837 B2  
APPLICATION NO. : 14/061187  
DATED : January 19, 2016  
INVENTOR(S) : Keijiro Omoto et al.

Page 1 of 1

It is certified that error appears in the above-identified patent and that said Letters Patent is hereby corrected as shown below:

In the specification

Col. 1, lines 7-9, reads:

"This is a Continuation Application of PCT Application No. PCT/JP2012/055186, filed February 27, 2013, which was published under PCT Article 21(2) in Japanese."

should read:

This is a Continuation Application of PCT Application No. PCT/JP2013/055186, filed February 27, 2013, which was published under PCT Article 21(2) in Japanese.

Signed and Sealed this  
Nineteenth Day of April, 2016

Michelle K. Lee  
*Director of the United States Patent and Trademark Office*